United States Patent [19]

Zimet-Sternberg et al.

[11] Patent Number: 5,773,794
[45] Date of Patent: Jun. 30, 1998

[54] METHOD FOR MAKING PERMANENT DENTAL ACRYLIC PARTS WITHOUT THE USE OF A DENTAL FLASK

[76] Inventors: Lilian Zimet-Sternberg; Alberto Sternberg, both of AV. Garibaldi 1969/603, Montevideo, Uruguay, 11800

[21] Appl. No.: 570,694

[22] Filed: Dec. 11, 1995

Related U.S. Application Data

[60] Continuation-in-part of Ser. No. 457,463, Jun. 1, 1995, Pat. No. 5,545,875, which is a division of Ser. No. 960,860, Oct. 14, 1992, Pat. No. 5,444,218.

[30] Foreign Application Priority Data

| Oct. 23, 1991 | [UY] | Uruguay | U-2974 |
| Oct. 23, 1991 | [UY] | Uruguay | 23305 |
| Dec. 13, 1994 | [UY] | Uruguay | 23869 |

[51] Int. Cl.⁶ .............................. A61C 13/14; F27D 7/02
[52] U.S. Cl. ........................................... 219/440; 433/32
[58] Field of Search ................................... 219/431, 440; 99/408; 433/25, 32

[56] References Cited

U.S. PATENT DOCUMENTS

| Re. 7,272 | 8/1876 | McDermut . |
| 320,980 | 6/1885 | Spyer . |
| 1,440,826 | 1/1923 | Hager . |
| 2,691,090 | 10/1954 | Vischer, Jr. . |
| 2,984,171 | 5/1961 | Lee, Sr. . |
| 3,194,662 | 7/1965 | Nelson . |
| 3,604,895 | 9/1971 | MacKay . |
| 3,609,296 | 9/1971 | Blair . |
| 3,973,481 | 8/1976 | Mies . |
| 4,362,148 | 12/1982 | Luebke et al. . |
| 4,771,162 | 9/1988 | Schatz et al. . |
| 5,444,218 | 8/1995 | Zimet-Sternberg et al. . |
| 5,545,875 | 8/1996 | De Sternberg et al. ............... 219/440 |

FOREIGN PATENT DOCUMENTS

| 111135 | 8/1940 | Australia . |
| 852117 | 8/1952 | Germany . |
| 1207994 | 10/1970 | United Kingdom . |
| 23305 | 10/1991 | Uruguay . |
| U-2974 | 10/1991 | Uruguay . |
| 13235 | 5/1992 | Uruguay . |
| U-1505 | 5/1992 | Uruguay . |

OTHER PUBLICATIONS

Leaflet for Biolon, by Caulk, Crown & Bridge Resin (about 1972).
Leaflet for Vitapan K+B, Vita Zahnfabrik, Bad Sackingen, Germany (between 1988 and end of 1990).
Leaflet for SR–ISOSIT–N of IVOCLAR, a subsidiary of Vivadent, Lichtenstein (about 1987).
Leaflet for Vitapan Monopast, Sudenco s.r.l., Montevideo, Uruguay (betweeen 1988 and end of 1990).
Leaflet for Vita–K+B 93K, Vita Zahnfabrik, H.Rauter GmbH & Co. KG, Bad Sackingen, Germany (between 1988 and end of 1990).
Leaflet for Cristal Major ND, Laboratorio Odontologico S.C. (about 1989 or Jan. 1990).
Leaflet for Vita Zeta (L C) Light Curing Composite (about 1995).

*Primary Examiner*—Teresa J. Walberg
*Assistant Examiner*—J. Pelham
*Attorney, Agent, or Firm*—Fisher, Christen & Sabol

[57] ABSTRACT

Dental parts which are permanently installed in the mouth such as acrylic teeth or jackets, bridges, crown veneers, acrylic crowns, crowns with an acrylic face or coating, and other permanent dental restorations containing acrylic are produced quickly and without substantial distortion or breakage without the use of a dental flask. Rock plaster is formed into a nest-shaped piece. The nest may be a vertical nest or horizontal nest which has a generally centrally located hollow portion or cavity having an open top. A dental part, made of wax, may then be inserted into the cavity and pressed by hand into the surface of the rock plaster to make or form an impression of the wax part within the inside surface of the nest. After the rock plaster dries or cures, the wax may be melted and removed from the nest. Heat-curable acrylic may then be dripped or poured into the hollow portion of the nest where it covers and fills the impression left by the wax dental part. The heat-curable acrylic in the nest may be cured without the use of a dental flask by indirect heating. The nest containing the heat-curable acrylic is submerged in ambient water within an open-topped curing container. The open-topped curing container is submerged in preheated water so that the top of the curing container is above the level of preheated water. The preheated water is maintained at acrylic curing temperatures and pressures to indirectly heat and cure the dental part without scorching or distorting it.

21 Claims, 6 Drawing Sheets

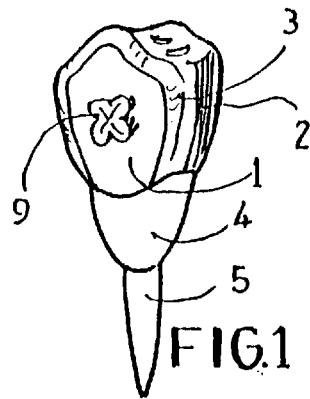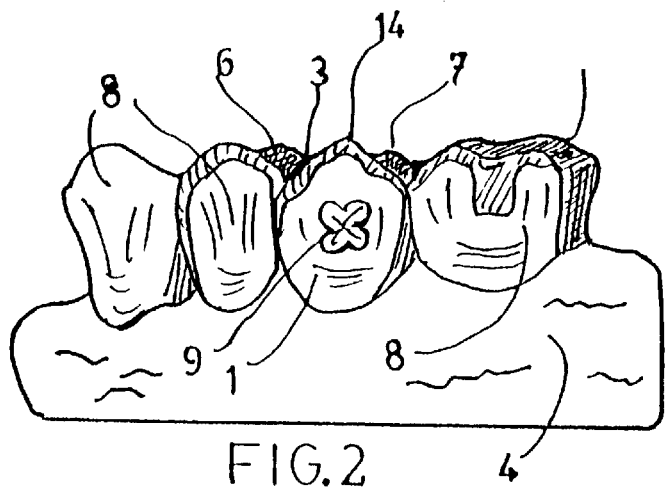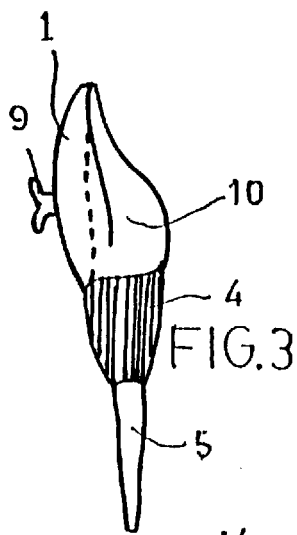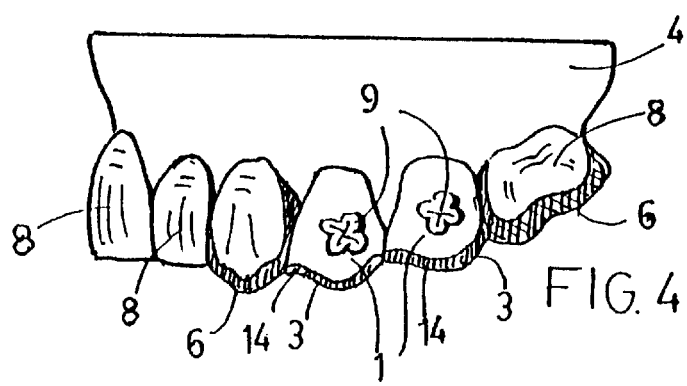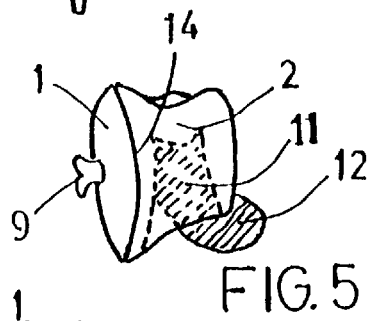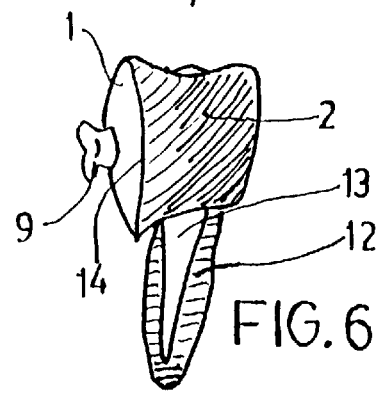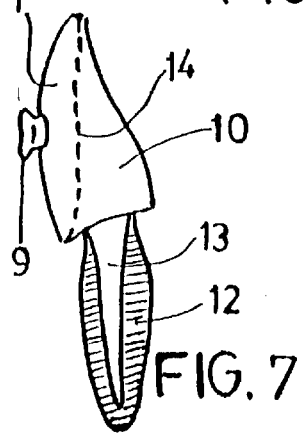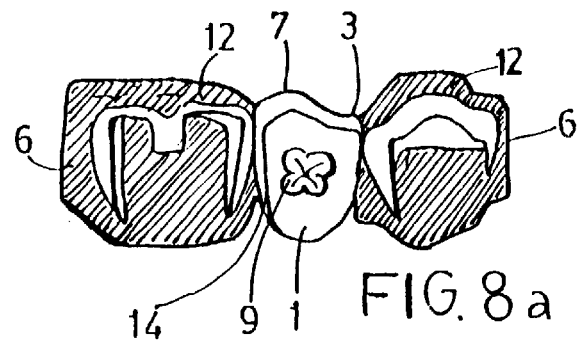

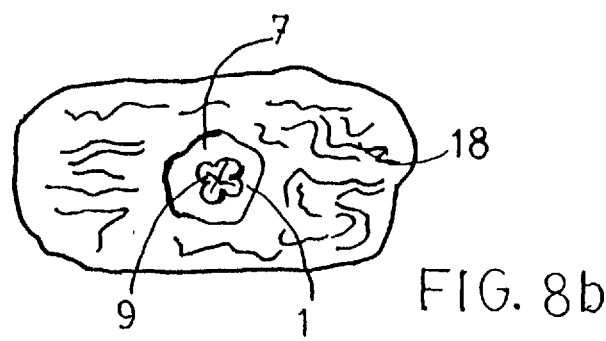
FIG. 8b
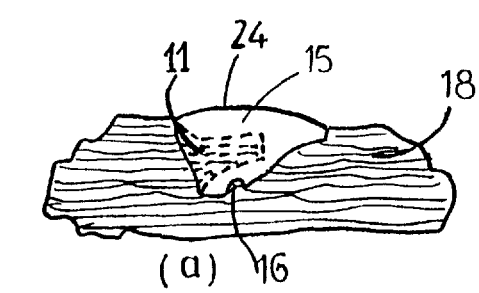
(a)
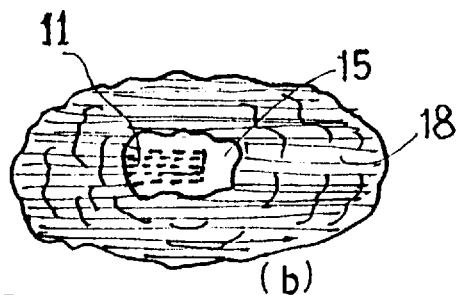
(b)
FIG. 9
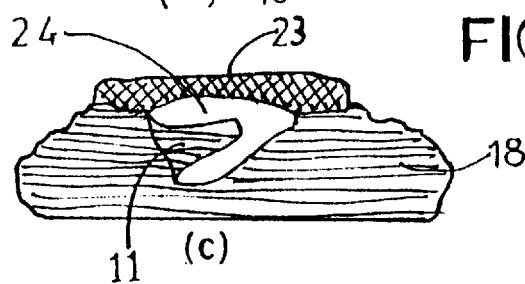
(c)
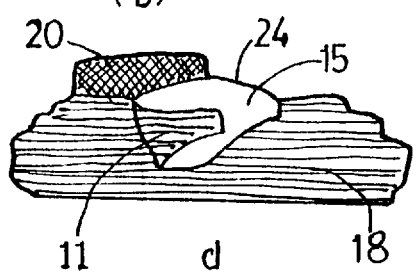
d
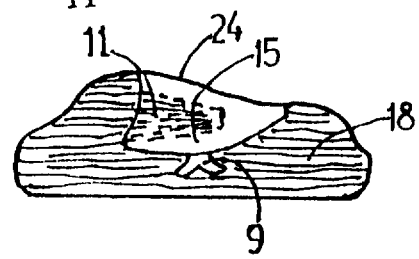
FIG. 10
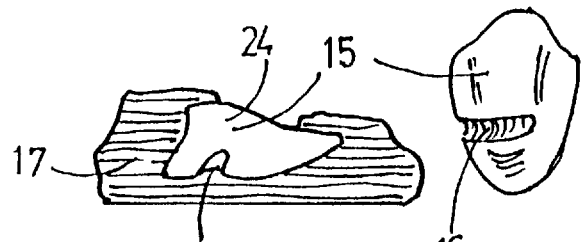
FIG. 11
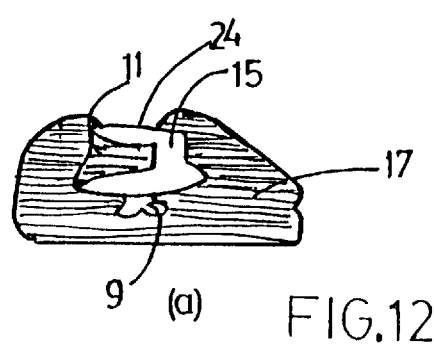
(a)
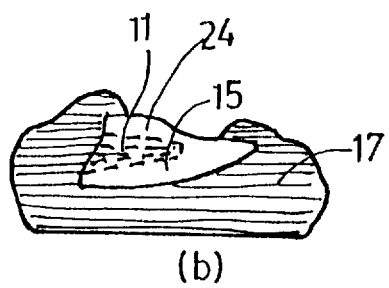
(b)
FIG. 12

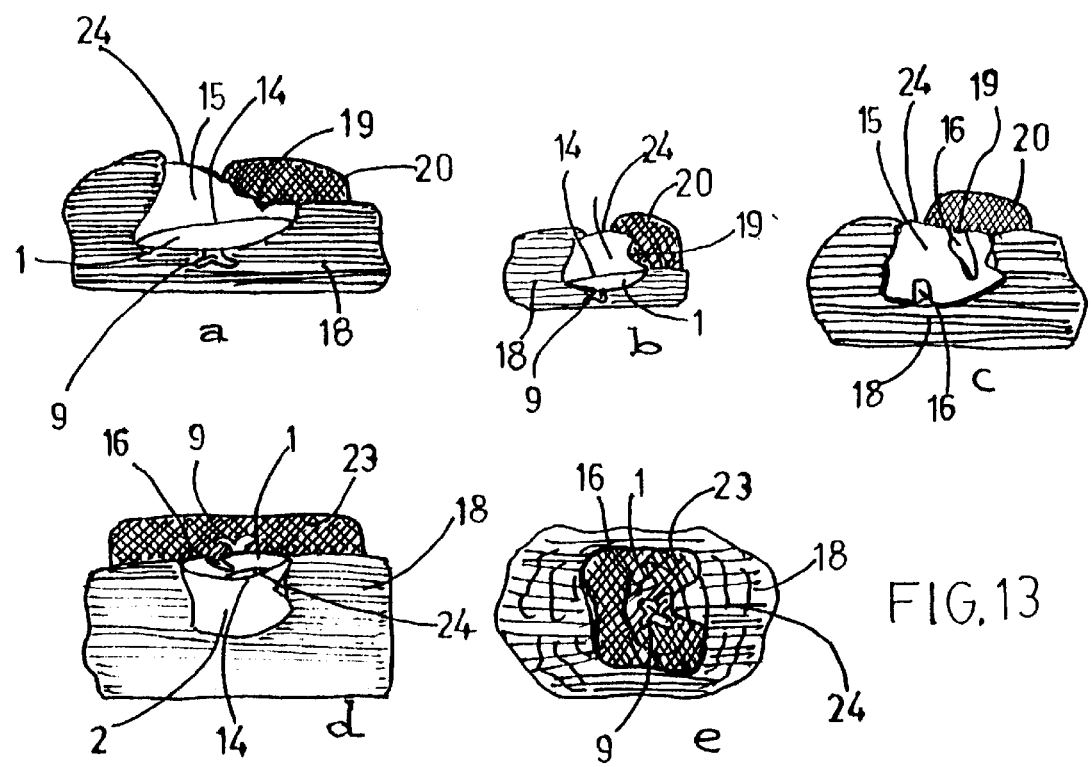
FIG. 13
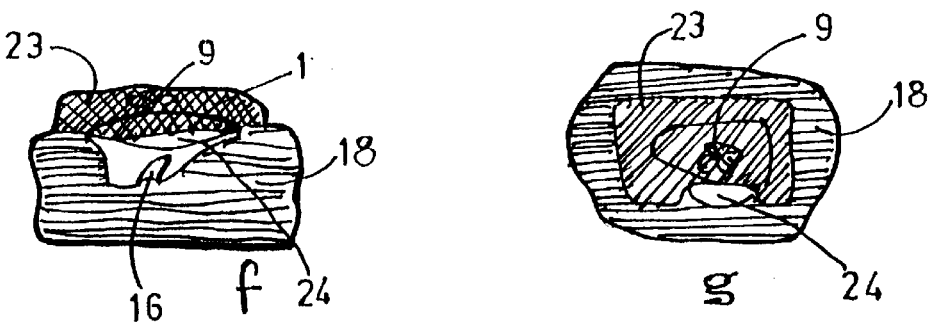
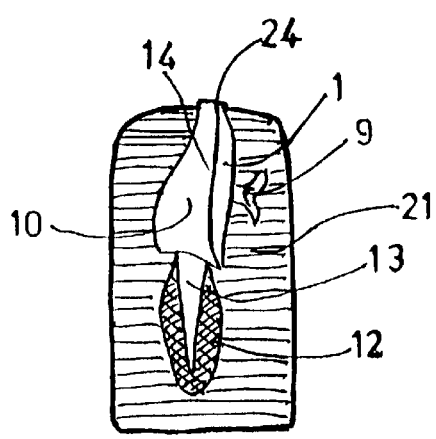
FIG. 14
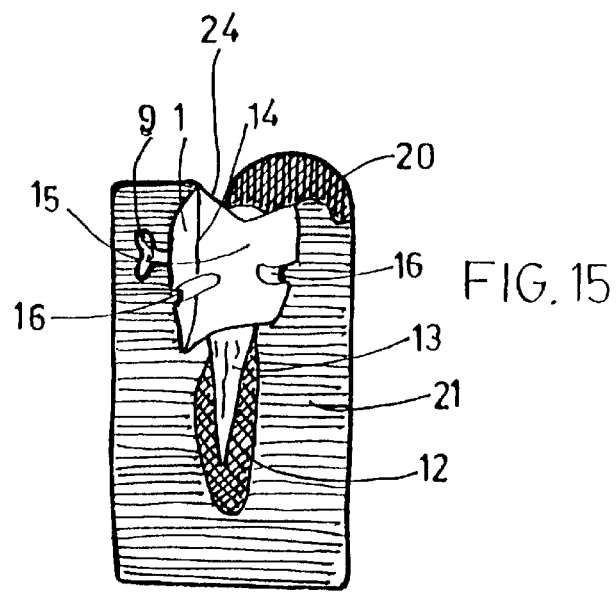
FIG. 15

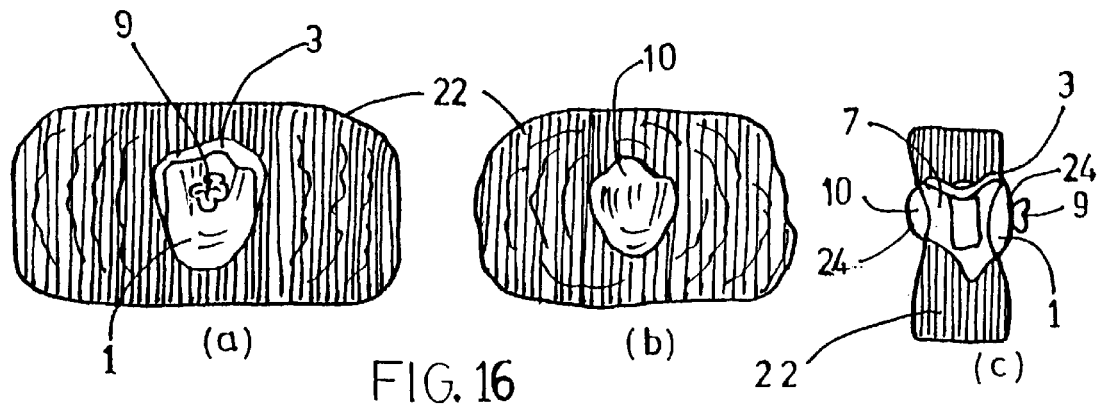
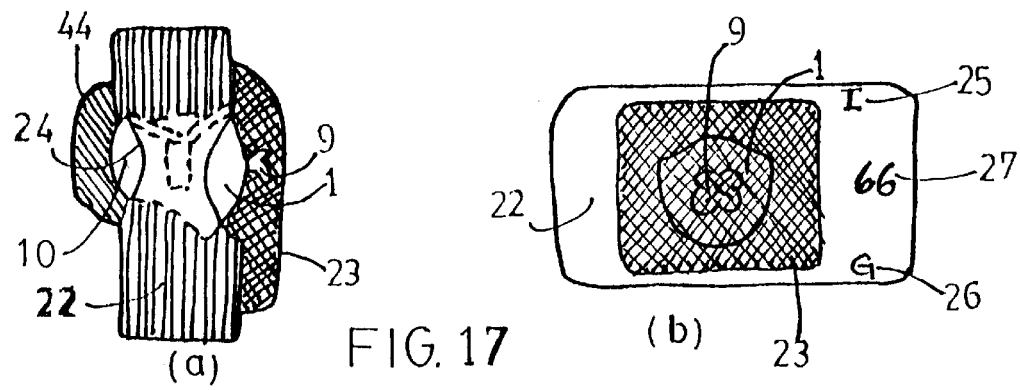
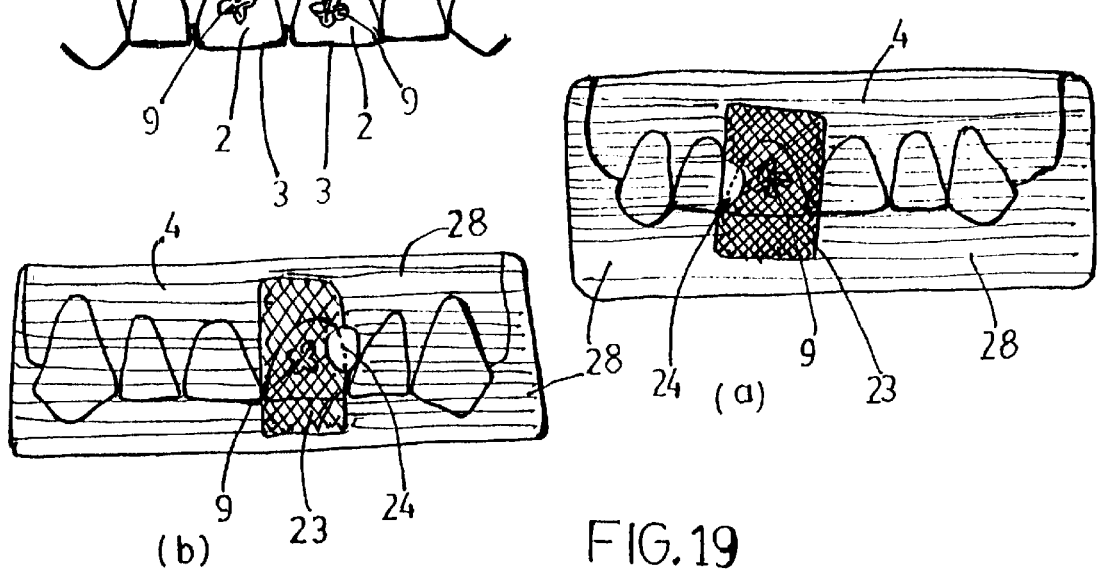

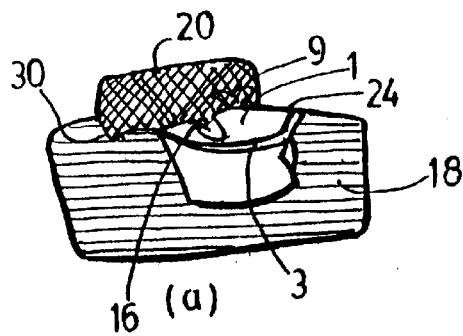
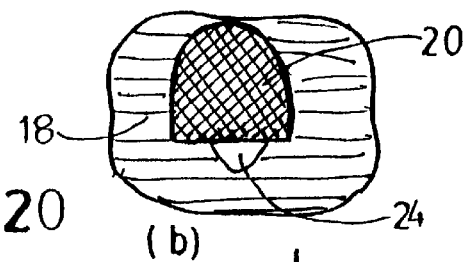
FIG. 20
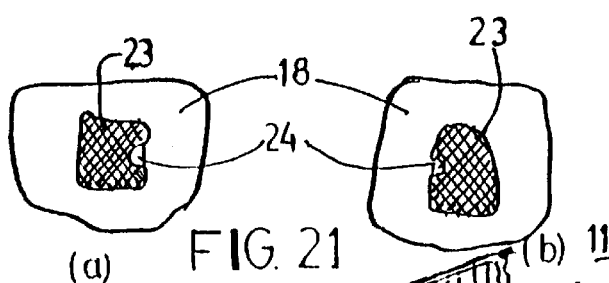
FIG. 21
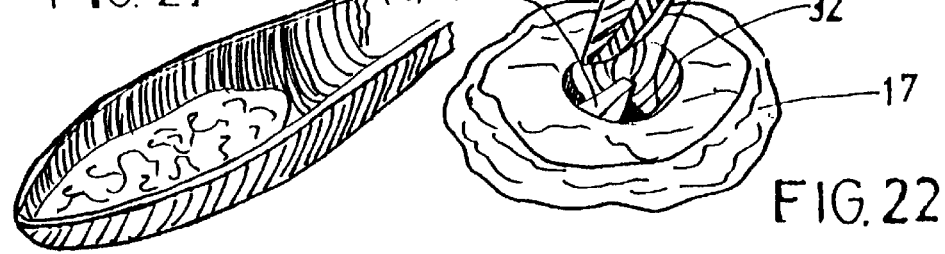
FIG. 22
FIG. 23
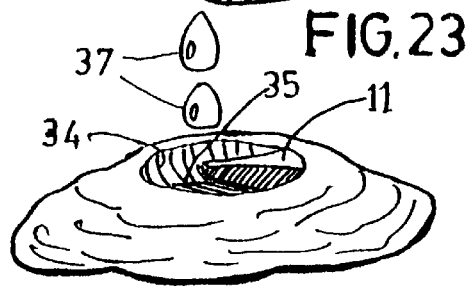
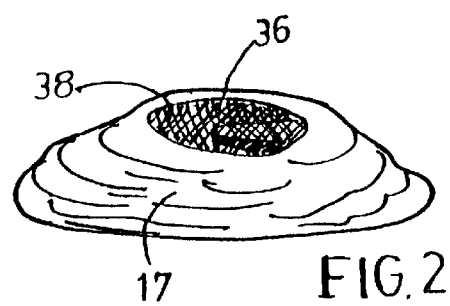
FIG. 24
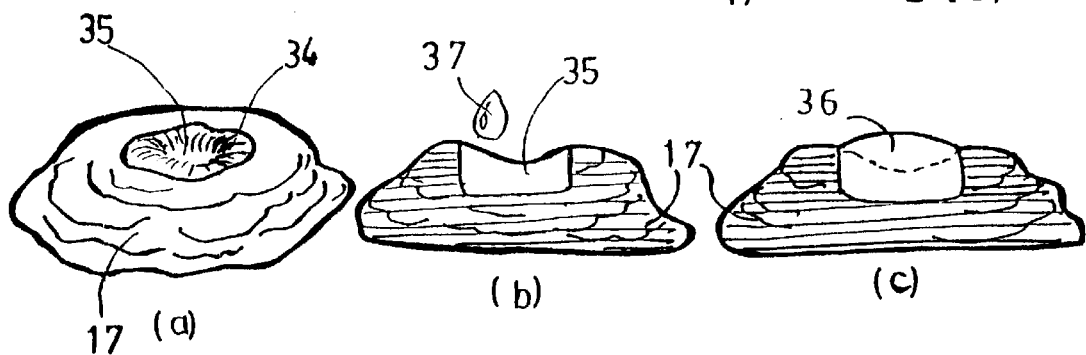
FIG. 25

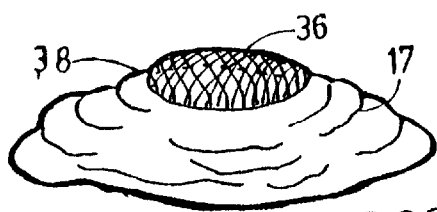
FIG. 26
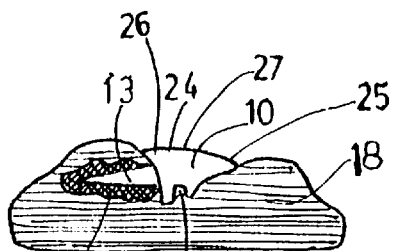
FIG. 27
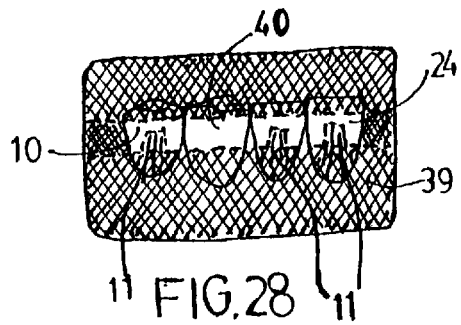
FIG. 28
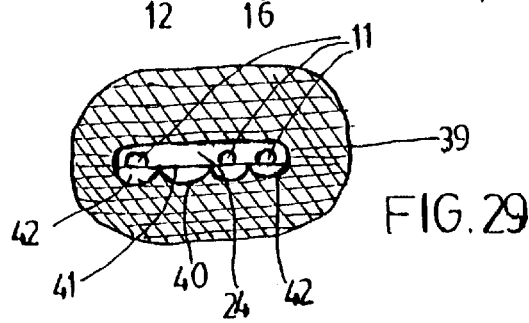
FIG. 29
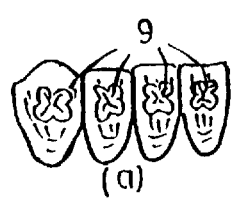
(a)
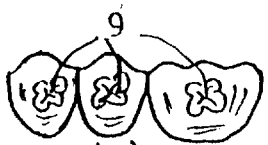
(b) FIG. 30
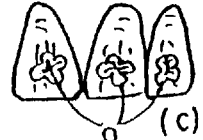
(c)
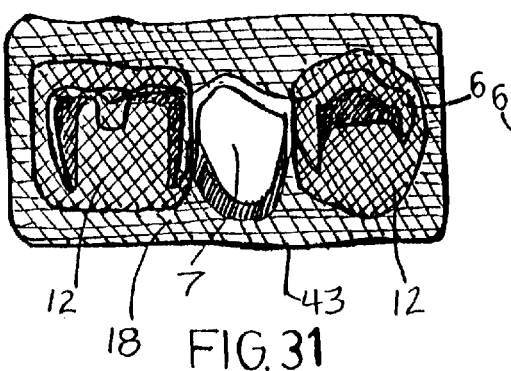
FIG. 31
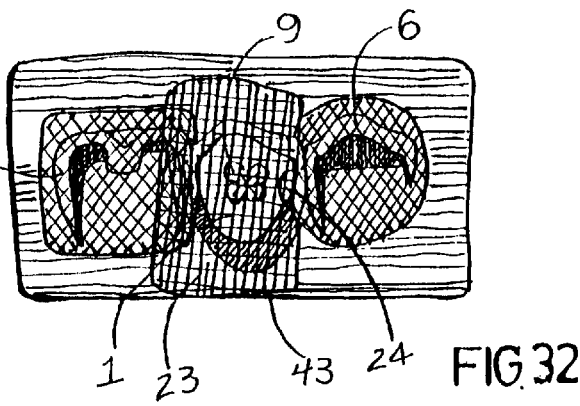
FIG. 32
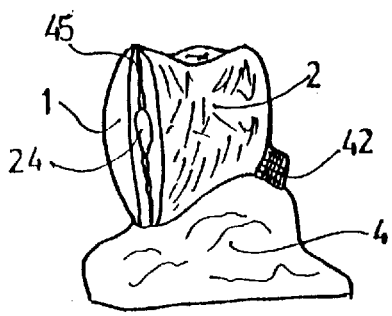
FIG. 33
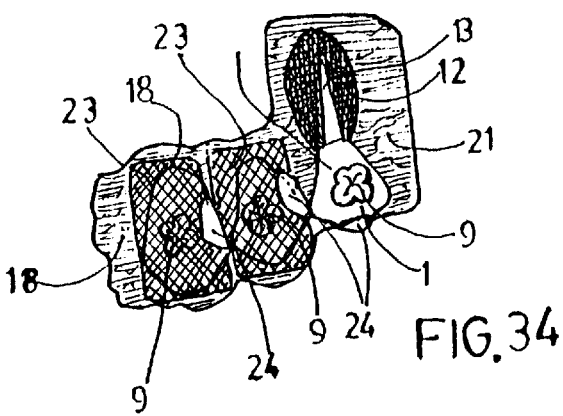
FIG. 34

மற்றும்...

METHOD FOR MAKING PERMANENT DENTAL ACRYLIC PARTS WITHOUT THE USE OF A DENTAL FLASK

RELATED APPLICATION

This application is a continuation-in-part of our U.S. application Ser. No. 08/457,463, filed Jun. 1, 1995, now U.S. Pat. No. 5,545,875, which is a divisional application of U.S. application Ser. No. 07/960,860, filed Oct. 14, 1992, now U.S. Pat. No. 5,444,218.

FIELD OF THE INVENTION

The present invention relates to the production of permanent dental parts which contain heat-cured acrylic, such as acrylic teeth or jackets, bridges, crown veneers, and acrylic crowns without using a dental flask.

BACKGROUND OF THE INVENTION

Dental flasks are conventionally used in the production of permanent dental parts which are fixedly retained in the mouth, such as acrylic teeth or jackets, bridges, and crowns. During the pressing stage and the opening stage of the flask process fracturing of plastic or porcelain teeth and other dental parts frequently occurs. In addition, the flask process is time-consuming and requires considerable physical strength for pressing of the flask in a vise. The flask process often results in a change in the vertical dimension of the dental part when pressing is performed which adversely affects its fit in the mouth.

We are against the use of a dental flask due to these disadvantages:

1. It takes much time in using it. (almost 4 hours)
2. It takes more plasters: Rock and Stone.
3. A third of the heat-curable acrylic is necessarily lost upon working it so as to avoid the porosity or wrong adjustment of the several pressing steps. With our method, the execution of a nest is made of rock plaster, takes approximately from two to four minutes and needs very little plaster (less than a third part that is used for dental flasks, that is about 10 grams) and only 0.6 grams of heat-curable acrylic are used.
4. With the use of a dental flask, the occlusal morphology changes, due to the position of the counterpart of the dental flask, that when it is not properly located, it is wrongly pressed and then modifies the occlusal morphology.
5. The vestibular thickness of the acrylic veneer of an acrylic crown, of the pivots, and of the fixed bridges, are modified by the same motive of the previous paragraph.
6. The acrylic veneer are moved in the counterpart during the pressed and are mixed with the plaster of the counterpart in the flask. (With our method is not necessary the pressing with a vise).
7. The edges do not remain well adapted by the isolating liquid because this allows a small separation as it has a minimum thickness. With our method isolating liquid is not required.
8. The approximal contact points are lost by the isolating liquid and by the mixture among the heat-curing acrylic and the plaster in the pressing. With our method the approximal contact points are not lost because the plaster does not adhere to the heat-curable acrylic.
9. When preparing heat-curable acrylic, we have to wait until the elastic stage is obtained to pack a dental flask in, we put on the veneer of an acrylic crown (opaqued), we press it with a vise and when we open it we see how the color remained because the vestibular face has very little thickness for the acrylic, if the color is different, we have to draw it, and prepare again the mixture of heat-curable acrylic until the color is correct, (the waiting for the polymerization until the elastic stage varies from 10 to 25 minutes.) With our method we can prepare the heat-curable acrylic in the moment, if happens that the color is diffuse as happened in the flask, we can remove it immediately and to add another tone without having to wait for the polymerization.
10. If we put the elastic heat-curable acrylic of a tone/color of dentine, we press it and cure it during 20 minutes. After the curing we cool the flask for 8 minutes and we open, without eliminating the work, we file the incisal part to put the elastic heat-curable acrylic, we press and cure again for another 20 minutes. With our method we put the dentine and incisal tone/color at the same time, and we cure immediately it with the processor apparatus for 15 minutes.
11. To rebase again an edge, we have to put it back in the flask, which takes much time. The only solution to avoid the use of the flask is to use selfcurable acrylic. Actually, in mouth the selfcuring acrylic irritates the mucous and retains the bacterial plate that provokes pyorrhea and/or the loss of this dental piece. With our method can be rebased with heat-curable acrylic on the model or in mouth and it cures immediately, for 15 minutes.
12. In the flask the elastic pigment overflows due to the pressing and its curing takes about 15 minutes. With our method the pigment remains very well located and is cure in 5 minutes with or without nests.
13. The preparation in heat-curing acrylic to pack with plaster in a flask takes more time, as before making the packing we have to verify if the color is the proper, it is packs, or if there is no need to repeat the preparation.

With our method the color is prepared in the moment; if we verify that the color is not the correct one we remove it and prepare it again immediately and we can see the mixture combining with other tones until the correct color is obtained.

14. Very often the odontologists and the patients complain because they cannot have the forms and color as planned.
15. Once the work is finished (a veneer for an acrylic crown or a fixed metal bridge), at last moment we see in the metallic part an open pore, we have to burn the acrylic already cured to weld it and we have to pack it back in the flask, and we cannot deliver the work that day by lack of time. With our method we can finish it on time, that is to weld the bridge or the crown and to improve the heat-curable acrylic of the requested color.
16. In order to color a neck we have to put it back in flask. With our method we can solve it immediately without accomplishing nests.
17. Any detail that appears in a given work at the moment of making it with the use of flask is impossible to solve. With our method can solve any detail immediately without damaging the work.
18. In order to make each work, it has to be put in flask to eliminate the wax, to prepare the heat-curable acrylic and to pack it, specially for that work and to cure it in individual form. With our method all kinds of works can be made at the same time that the nests are made to eliminate the white waxes, to add the heat-curable acrylic and to cure it.

In the present invention, dental parts which are permanently fixed or cemented in the mouth are made without the use of a dental flask from the stage of the temporary tooth made of white wax through the stage of finishing the part in conventional heat-curable acrylic polymer.

SUMMARY OF THE INVENTION

The present invention provides a procedure for the production of permanent dental parts which comprise heat cured acrylic. The procedure accelerates and simplifies the production of dental parts which are permanently installed in the mouth such as acrylic teeth or jackets, bridges, crown veneers, acrylic crowns, crowns with an acrylic face or coating, and other permanent dental restorations containing acrylic. In embodiments of the invention, rock plaster is formed into a nest-shaped piece. The nest may be a vertical nest or horizontal nest which has a generally centrally located hollow portion or cavity having an open top. Other pieces for making the dental parts include multiple and duplicate nests, mixed nests or combinations of vertical nests and horizontal nests, vertical middle nests and entire nests, half retainers, and entire retainers. Each of these pieces may be made in rock plaster.

In embodiments of the invention, a dental part, made of wax, may then be inserted into the cavity of a nest and pressed by hand into the surface of the Rock plaster to make or form an impression of the wax part within the inside surface of the nest. After the Rock plaster dries or cures, the wax may be melted with boiling or hot water and optional soda. The melted wax is removed from the nest and the nest may be cleaned and treated for receiving the heat-curable acrylic. Fluid, heat-curable acrylic may then be dripped or poured into the hollow portion of the nest where it covers and fills the impression left by the wax dental part. The heat-curable acrylic in the nest or the opening in the nest may be uncovered or optionally partially or completely covered with plaster prior to curing.

The curing of the acrylic is performed without the use of a dental flask by indirect heating using a curing container and curing vessel as disclosed in our U.S. Pat. No. 5,444,218. Thus, the nest with the heat-curable acrylic inside it may be varnished and dried at room temperature. The inlet of the nest may be covered with plaster of paris and then the nest may be placed in the curing container with ambient temperature water for heat curing of the acrylic in the apparatus of U.S. Pat. No. 5,444,218. The curing container may be filled with ambient water to a level which covers the nest after submerging the curing container in the pressure vessel. The curing container is supported in the pressure vessel so that the top edge of the curing container is above the level of preheated hot water held by and heated by the heating means in the vessel. The ambient temperature water in the curing container is heated up to a temperature sufficient to heat cure the acrylic dental part within the nest. The water in the curing container is heated by the pressure vessel's preheated hot water which surrounds the open topped, curing container. The heat curing may be conducted at a pressure of 3.5 bars and a temperature of about 90° to about 100° C. After heat-curing, the heat-cured acrylic dental part may be removed from the nest, cleaned and polished.

BRIEF DESCRIPTION OF THE DRAWINGS

FIG. 1 is a perspective view of an acrylic crown 2 with plastic mask 1 with grip 9 (mounted on a die 4 and a dowel pin 5) showing joining among the plastic mask and the metal with white wax 3. (Dowel pins are made in bronze and it is only used to make the work).

FIG. 2 is a side view of a fixed bridge 6 with a plastic mask 1 and grip 9 mounted on a die 4 to make the work.

FIG. 3 is a side view by approximal of a plastic mask 1 with a grip 9 with white wax adapting the lingual or palatine face 10 with the work assembled on a die 4 and dowel pin 5.

FIG. 4 is a fixed bridge 6 with two plastic masks 1 and grip 9 mounted in a die 4.

FIG. 5 is a side view of acrylic crown 2, equal to FIG. 1 withdrawn of the die and covered with coating 12 in the internal part 11.

FIG. 6 is an acrylic crown 2 on pin 13 whose pin is covered with coating 12.

FIG. 7 is a side view of a pivot. It is a pin with stump covered with a jacket with plastic mask 1 and white wax and whose pin is covered with coating 12.

FIG. 8a is a fixed bridge of the FIG. 2 withdrawn from the model-die to cover the metallic part with coating 12.

FIG. 8b is a top view of a horizontal nest 18 made in rockplaster, of a fixed bridge leaving the pontic piece 7 with plastic mask 1 uncovered with grasp 9.

FIG. 9a is a sectional side view of a horizontal nest 18 leaving the uncovered vestibular face 24 of a wax pattern 15.

FIG. 9b is a top view of a horizontal nest 18 with the wax pattern 15 with the vestibular face uncovered wherein reference 11 indicates that the rockplaster fills the internal part of the jacket.

FIG. 9c is a side sectional view of a horizontal nest 18 with an entire retainer 23 made in rockplaster, that covers the uncovered vestibular face as shown in FIGS. 9a and 9b.

FIG. 9d is a sectional side view of a horizontal nest 18 with half retainer 20 that covers partially the vestibular face 15 and the uncovered face 24 that receive the filling by dripping of the present invention.

FIG. 10 is a sectional side view of a jacket in wax with vestibular plastic mask 1 with grip 9 made in self curable acrylic within a horizontal nest 18 leaving the uncovered face 24 by lingual or palatine.

FIG. 11 is a sectional view of a jacket in wax 15 without a plastic mask that shows the marks of a hook 16 in the vestibular face located in a horizontal nest 18.

FIG. 12a is a sectional view of a jacket in white wax 15 of a premolar with plastic mask 1 and grip 9 within a horizontal nest with occlusal coating 17 of the present invention. (In this case the occlusal coating is made in the horizontal nest and in rockplaster).

FIG. 12b is a side sectional view of an incisive 15 without a plastic mask, within a horizontal nest 17 leaving an uncovered face 24 by lingual or palatine of the present invention.

FIG. 13a is a side sectional view of a jacket in wax 15 with plastic mask 1 and grip 9 that is inlaid in a horizontal nest 18 leaving the lingual or palatine face uncovered 24 with marks of the occlusion 19 with half retainer 20 leaving a third of uncovered face for the filling by dripping.

FIG. 13b is a side sectional view of a jacket in wax 15 with plastic mask 1 and grip 9 of a premolar or molar, leaving the occlusal face 19 and lingual or palatine uncovered 24 with half retainer 20, and making a third of uncovered face for the filling by dripping.

FIG. 13c is a side sectional sight of a jacket in wax 15 without plastic mask with marks of a hook 16 within a horizontal nest 18 with the same characteristics of FIG. 13b.

FIG. 13d is a sectional view showing an acrylic crown 2 with a plastic mask 1 and grip 9 with a mark of a hook 16 within a horizontal nest 18 similar to FIG. 13c, changing the position of the piece to work and the placement of the third of uncovered face 24.

FIG. 13e is a top view of the FIG. 13d embodiment with a third of uncovered face 24 by mesial for the filling by dripping of the present invention.

FIG. 13f is a side sectional view of a horizontal nest 18 of a jacket in wax with plastic mask 1 and grip 9 with marks of hooks 16 by lingual or palatine, leaving the uncovered vestibular face to be covered by an entire retainer 23 made in rockplaster, and then leaving a third uncovered face 24 by distal or mesial for the filling by dripping.

FIG. 13g is a top view of the FIG. 13f embodiment.

FIG. 14 is a sectional view of a pivot incisive cover with wax 10 and a plastic mask 1 and grip 9; no. 14 shows the joined edge of the wax 10 and the plastic mask 1, no. 12 is the coating that covers the pin 13 of the pivot. All of the set is introduced in a vertical nest 21 also made in rockplaster, leaving the occlusal face 24 uncovered.

FIG. 15 is a sectional view of a pivot in wax 15 of a premolar with plastic mask 1 and grip 9 with mark of a hook 16 by lingual or palatine and vestibular whose pin 13 is covered with coating 12 within an entire vertical nest 21 leaving the occlusal face 24 uncovered, covering it with a half retainer 20 for the filling by dripping of the present invention.

FIG. 16a is a top view of a vertical middle nest 22 showing the wax border 3 that joins the plastic mask with the metal of a jacket with occlusal face of metal.

FIG. 16b is a top view of the lingual or palatine side of a vertical middle nest 22 with the wax 10.

FIG. 16c is a top view of a vertical middle nest 22 showing the two uncovered faces 24 for vestibular and lingual or palatine.

FIG. 17a is the same sectional view of the FIG. 16c by vestibular is placed an entire retainer 23 and the lingual or palatine face is for filling by dripping. The wall 44 is used for the filling by dripping by the zone of the entire retainer 23 leaving a third uncovered face.

FIG. 17b is a frontal view of the vertical half nest 22 that shows the marks of the position of the pieces to work as incisal 25 and gingival 26 and the color of dentine 27.

FIG. 18 shows the two preparation acrylic crowns 2 with plastic mask 1 and grip 9 mounted on the die 4 in which are seen the wax edges 3.

FIGS. 19a and b show the vertical nest duplicated 28 of both acrylic crowns 2 of FIG. 18 leaving the uncovered vestibular faces and above these there is placed an entire retainer 23 leaving a third of uncovered face 24 by distal of both acrylic crowns 2 for the filling by dripping of the present invention.

FIGS. 20a and b are sectional side views of a horizontal nest 18 of an acrylic crown in white wax 1 with half retainer 20 that is fastened with an undermined 30.

FIGS. 21a and b are top views of the horizontal nests 18 with entire retainers 23 leaving a third of uncovered face 24 for the filling by dripping of the present invention.

FIG. 22 is a horizontal nest with occlusal coating 17. Once the white wax 1 is eliminated, the hollow 34 is seen and with the scalpel 33 then the rest that remains by the edge of the hollow is eliminated.

FIG. 23 is a perspective view of the canoe shaped spatula 29 with the heat curable monomer and whose drops 37 fall in the hollow 34 of the horizontal nest with occlusal coating 17.

FIG. 24 is a perspective view of a horizontal nest 18 with occlusal coating 17 filled with heat curing acrylic 36 up until the top edge 38 of the hollow 34.

FIG. 25a is the following step of FIG. 24 with the acrylic already poured and with the sunked portion 35.

FIG. 25b is a side view of the heat curable acrylic sunked portion 35 and is returned to be filed by a heat curable liquid drop 37.

FIG. 25c is the following step of the FIG. 25b with the new filled portion of the heat curable acrylic 36.

FIG. 26 is a perspective view showing a nest completely filled with heat curable acrylic 36.

FIG. 27 is a sectional side view of a pivot in a horizontal nest 18 with the uncovered vestibular face 24 in which it is shown the place to pigment the incisal edge 25 and the edge gingival 26 and the color of dentine 27.

FIG. 28 is a frontal view of a multiple horizontal nest 39 with occlusal coating, the one which has a wax bridge leaving the lingual or palatine uncovered 24 for the filling by dripping.

FIG. 29 is a top view of a multiple horizontal nest 39 of a bridge and with an internal reinforcement of stainless steel wire 41.

FIGS. 30a, b, and c are frontal views of the grips 9 for each plastic mask 1 of anterior and posterior of future acrylic bridges.

FIG. 31 is a frontal view of a horizontal nest 18 with a fixed metal bridge 6 leaving the pontic piece 7 in vestibular discovered or the filling by dripping of the present invention.

FIG. 32 is a frontal view of a fixed metal bridge 6 with pontic piece 7, plastic mask 1 and grip 9 in a multiple horizontal nest 39, and above the pontic piece there is placed an entire retainer 23 with a third of uncovered face 24 for the filling by dripping of heat curable acrylic.

FIG. 33 is a side view of an acrylic crown 2 with a plastic mask 1 on the die 4 that is fixed with self curable acrylic 42, and the plastic mask 1 is fixed with pink wax 45. The filling by dripping is made by distal in a third of uncovered face 24.

FIG. 34 is a frontal view of a mixed nest made in rockplaster for a fixed bridge with plastic mask 1 and grip 9. Shown by sectioning are the two first pieces of the bridge and there is made a horizontal nest 18 with entire retainers 23 with a third of uncovered face 24 for the two pieces and it is joined with an entire vertical nest 21 whose occlusal face uncovered 24 is for the filling by dripping of the present invention.

DETAILED DESCRIPTION OF THE INVENTION

It is a new method to finish the white colored acrylic part for the future dental restorations without the use of flasks.

The white wax pattern is substituted by white heat-curable acrylic for dental use and it is necessary to make two kinds of nests that are made of rock plaster and are called:

1) Horizontal nests.
2) Vertical nests.

Corresponding for the completion of:

1) Jacket made in white wax.
2) Jacket made in white wax and with retainer.
3) Jacket made in white wax with plastic mask.
4) Jacket made in white wax with plastic and with retainer.
5) Pivot made in white wax.
6) Pivot made in white wax and with retainer.

7) Pivot made in white wax with plastic mask.

8) Pivot made in white wax with plastic mask and with retainer.

9) Fixed acrylic bridge made in white wax.

10) Fixed acrylic bridge made in white wax with internal reinforcement.

11) Fixed acrylic bridge made in white wax with plastic mask.

12) Fixed acrylic bridge made in white wax with plastic mask with internal reinforcement.

The veneers of:

13) Acrylic crown made in white wax.

14) Acrylic crown made in white wax and with retainer.

15) Acrylic crown made in white wax with a plastic mask and with retainer.

16) Fixed metal bridge made in white wax veneers.

17) Fixed metal bridge made in white wax veneers and with retainer.

18) Fixed metal bridge made in white wax and with plastic mask with retainer.

Due to its hollow form, the preparation in rock plaster for the manufacture of our work is called nest. This hollow is used to fill the heatcurable acrylic by dripping. The heatcurable acrylic is prepared in fluid form which will fill by dripping through this hollow with a canoe shaped spatula and with the aid of a vibrator to which the respective nest was previously lent until it is completely filled, it is allowed to rest, and then it will be processed to heat to 90° C. and with 3 and ½ pressure bars with the ELECTRICALLY HEATED APPARATUS U.S. Ser. No. 07/960,860 (U.S. Pat. No. 5,444,218 issued Aug. 22, 1995) of our property to make the total boiling during 15 minutes and the cooling is immediate. The disclosures of our U.S. application Ser. No. 07/960,860 and our U.S. Pat. No. 5,444,218 are herein incorporated by reference in their entireties.

As disclosed in U.S. Pat. No. 5,444,218, the electrically heated pressure processor apparatus comprises a vessel for boiling or heating water, a resistance heating means for heating water held in the vessel, means for supplying compressed air to the vessel, one or more curing containers, and a foldable, perforated table for supporting the curing containers in the vessel. The curing container is filled with water to a level which covers the plaster nest after submerging the container in the vessel. The table supports the curing container in the vessel so that the top edge of the curing container is above the level of water held by and heated by the heating means in the vessel. This arrangement permits: (1) heating of the water in the vessel to a temperature sufficient for heat curing of the acrylic dental part, and (2) then placement of the curing container with the water covered, acrylic-containing nest into the heated water to heat the water in the curing container without subjecting the acrylic dental part to burning. The resistance heating means is located below the table which supports the curing container. The use of a perforated table permits the circulation of the heated water around the curing container.

In this way we eliminate completely the use of dental flask, because these do not satisfy dental technician, or odontologist as the expected results are not obtained, at the same time that it takes many materials and working load.

Now,—We present a small chart on the place of the elimination of the dental flask:

---

White wax pattern. (WITH OR WITHOUT PLASTIC MASK) as we usually do.
WE SUBSTITUTED THE DENTAL FLASK TO MAKE NESTS.
FILLING BY DRIPPING OF HEATCURABLE ACRYLIC.
CURING STAGE IN THE PROCESSOR APPARATUS.
COOLING OF THE NESTS.
OPENING OF THE NESTS.
Filling and polishing as usual.

---

In summary:

The execution of the horizontal or vertical nests in rockplaster takes from 2 to 4 minutes.

The execution of retainers in rock plaster or on Paris or Stone plaster takes one minute.

The elimination of the white wax with hot water take three minutes, if they are more two nests it takes 5 minutes.

The preparation, filling by dripping of heatcurable acrylic until its hardening before making the boiling takes about 10 minutes.

The filling by dripping heatcurable acrylic on the hollows in more than seven nests (either of them) until it hardens takes 15 minutes. (Previous to the boiling).

It can be placed more than ten nests (anyone) inside of the curing container to make all on the same boiling. The nests with the heatcuring acrylic already filled and hardened, can be put inside the curing container in any position without they being affected or modified either by boiling water heat and/or the pressure of the processor apparatus, when curing them in a same boiling.

The boiling of thicker heatcurable acrylic needs 15 minutes and the boiling of thinner heatcurable acrylic takes about five minutes.

After the boiling, the work cured in heatcuring acrylic does not need rest, its cooling being immediate and takes from one to three minutes.

The removal from the cured work of the nests takes about 2 minutes.

The materials used for elaboration are:

Electrically heated processor apparatus U.S. Ser. No. 07/960.860 [U.S. Pat. No. 5,444,218 issued Aug. 22, 1995]. Property of LILIÁN ZIMET DE STERNBEG and ALBERTO STERNBERG.

Compressor.

Vibrator.

Stainless Steel Spatula, canoe shaped for acrylic dropping.

White Heatcuring Acrylic powders of different tones.

Heatcuring liquid monomer.

Plastic tooth, upper and lower sets

Opaquer.

Alginate.

Pins with head.

Selfcuring acrylic.

Pink and white wax.

Plasters: Paris, Stone, Rockplaster.

Coating. (Which is used to make metal casting).

Stainless steel wire.

Polishing articles to give bright.

Articulating paper.(carbon paper)

Cotton.

Paper napkins.

| GENERAL CLASSIFICATION: | | | |
|---|---|---|---|
| NESTS | HORIZONTAL: WITH RETAINERS: | 1) 2) 3) 4) | with occlusal coating. without occlusal coating. half entire. |
| | VERTICAL: WITH RETAINERS: | 1) 2) 3) 4) | without occlusal entire coating without occlusal half coating. half. entire. |
| FILLING BY DRIPPING | BY THE HOLLOWS: | | vestibular. palatine or lingual. mesial or distal occlusal |
| ARE CURED IN 5 MINUTES. ARE CURED IN 10 MINUTES. ARE CURED IN 15 MINUTES. | | | for all the required dental works it is used the processor apparatus, U.S. Ser. No. 07/960,860. [U.S. Pat. No. 5,444,218 ISSUED 8/22/1995] |

Now, we present a study of time to make the nests from the beginning with the filling by drip of the heatcurable acrylic until the final curing.

The nests in general take a minimum of 2 hours and 30 minutes.

The nests with retainer take 2 hours and 35 minutes.

The duplicated nests take 2 hours and 55 minutes.

The quicker jobs, without making nests take 1 hour and 15 minutes. The filling by dripping heatcurable acrylic on the original model in rockplaster is for the requested urgent works like the finishing of the veneer of an acrylic crown and several veneers of the fixed metal bridges with or without plastic mask.

The pigmentation, without making the nests (to darken, clarify the necks, give it to the dentine part of the plastic tooth or improve the incisal edges) takes 10 minutes (from the filling by dripping or by the adjustment of the heatcurable acrylic until it is cured).

The rebasings that are made on the original model take 15 minutes. (from the filling by dripping or adjustment of the heatcurable acrylic until it is cured).

The repairs without making nests take 15 minutes. (from the filling by dripping of the heatcurable acrylic until it is cured).

TEMPORARY PATTERNS OF WHITE WAX

There exists two forms of white wax patterns (for jackets, veneers of the acrylic crowns, of the pivots and of the fixed bridges):

1) in entire and molded white wax.

2) in white wax with plastic mask with the form and similar color of the natural teeth. (the plastic mask are made of upper or lower plastic teeth sets that are used to make dentures).

If plastic mask are needed, the internal retentions have to be done wider than usual, as if they would be like open arms to receive the heatcurable acrylic. After making the perforations, the sheen has to be eliminated from the peripheral contour of the plastic mask to give it a good finishing in heatcurable acrylic. Otherwise, a small separation will be noticed among the plastic mask and the acrylic. Afterwards, one has to complete the adaptation of the plastic mask with white wax.

IMPORTANT NOTICE: When a plastic mask is put, it is necessary to place it very well adjusting the gingival borders and the approximal sides. If it is unsuitable to put a plastic mask for any reason, it would be better to substitute the plastic mask making one of molded white wax.

IN ORDER TO DESCRIBE MORE CLEARLY OUR METHOD WE ATTACH THE FOLLOWING SUMMARY OF THE REFERENCE POINTS OF EACH FIGURE:

1-Plastic mask or plastic veneer or made in wax.
2-Acrylic crown.(or metal crown with veneer)
3-White wax edge.
4-Die.
5-Pin.
6-Metallic part of the fixed metal bridge.
7-Pontic piece of the fixed metal bridge (the main piece of a bridge).
8-Natural teeth.
9-Grips.
10-Palatine or lingual wax.
11-Internal Part.
12-Coating.
13-Spike or pin.
14-Edge of the plastic mask.
15-White wax pattern.
16-Marks of the hooks.
17-Horizontal Nest with occlusal coating.
18-Horizontal Nest without occlusal coating.
19-Occlusion marks.
20-Half retainer.
21-Entire vertical Nest.
22-Half vertical Nest.
23-Entire Retainer.
24-Uncovered Face or a third of uncovered face.
25-Color of the incisal edge.
26-Color of the gingival edge.
27-Color of the dentine.
28-Duplicated vertical nest.
29-Canoe-shaped metal spatula.
30-Undermined.
31-Approximal contact points.
32-Residues of white wax.
33-Scalpel.
34-Hollow.
35-Sunked heatcuring acrylic.
36-New refilling of the heatcurable acrylic.
37-Drop of heatcurable liquid monomer.
38-Edge of the hollow of the nest.
39-Multiple horizontal Nest.
40-Pontic piece of the bridge of heatcuring acrylic.
41-Stainless steel wire.
42-Selfcuring acrylic.
43-Rockplaster.
44-Lingual or palatine wall.
45-Pink Wax.

Notice: In the technical explanation the references to the drawings with figures are written as figure number, point or number of reference of the indicated topic. For example: (FIG. 2.16) that is FIG. 2, point or reference 16.

TECHNIQUE ON THE FINISHING OF THE WAXING OF THE WAX PATTERNS WITH OR WITHOUT PLASTIC MASK FOR THE JACKETS, ACRYLIC CROWNS, PIVOTS AND METAL OR ACRYLIC BRIDGES:

The technique consists in that the peripheral edges of the wax have to be waxed with very much attention (gingival, mesial, distal, occlusal and incisal) with or without plastic mask before making nests for:

JACKETS, PIVOTS AND FIXED BRIDGES IN HEATCURING ACRYLIC:

Once the white wax is ready with or without plastic mask it is not necessary to add more white wax.

THE VENEERS OF THE ACRYLIC CROWNS AND OF THE FIXED METAL BRIDGES:

For the wax veneer or the plastic mask (FIG. 1.1) of the acrylic crowns and of the fixed metal bridges (FIG. 2.1) more wax has to be added through the edges of the joint between the wax with or without veneer and the metallic part. (by the approximal sides and occlusals so that the rockplaster is not mixed with the heatcurable acrylic. (FIGS. 1.3 and 2.3)

TECHNIQUE FOR MAKING GRIPS ON THE VESTIBULAR FACES OF THE PLASTIC MASK BEFORE MAKING HORIZONTAL OR VERTICAL NESTS, WITH OR WITHOUT RETAINERS.

Before making the nests, grips for the vestibular faces have to be made so that the plastic mask be fixed in its place when receiving the fluid heatcurable acrylic. grips on each plastic mask have always to be make for jackets, veneer of the acrylic crowns, pivots, fixed metal and acrylic bridges (FIGS. 1.9 to 8.9)

In order to make a grip in the face of a plastic mask the sheen from its center has to be removed so that the selfcurable acrylic adhered better. Otherwise, if the sheen is not removed, the grips will release itself during the washing of the white wax or when dripping of fluid heatcurable acrylic.

To make the grips has to be used a selfcurable acrylic of diferent color.

The technique is very simple: a drop of selfcuring acrylic has to be put through the center of the veneer, (where the sheen was removed), allow it harden a little, press it with a sharp edged spatula through the center in order to open it toward both sides letting it as opened fins, as if it were an opened flower. (FIGS. 1.9 to 8.9)

If plastic masks are not used, there is no need to make grips. The grips take approximately 2 to 3 minutes of work, for one or more plastic masks.

For the fixed metal or acrylic bridges (all the veneers that are to be made), separate grips have to be made in order to facilitate the expulsion of the nest. An entire grip that retains more than one veneer has not to be made (FIG. 4.9), as during the opening of the nest the plastic mask will break or come out together with the grips removing themselves from the fixed metal bridge.

TECHNICAL TO AVOID THE DEFORMATION OF THE WAX PATTERN BEFORE MAKING NESTS.

1-The works with white wax with or without plastic mask with the model—die (white wax patterns) have to be submerged in tap water at room temperature for 2 minutes.

2-The wax patterns have to be soaped and rinsed with water profusely to decrease the superficial tension of the wax.

WHAT IS THE USE OF COATING AND WHEN DOES IT HAVE TO BE USED?

Common coating has to be used to protect the metallic parts, for example: the edges of the acrylic crown, on the pins of the pivots, the inlays or crowns with pins that are permanent pillars of a fixed bridge; these should be recovered with common coating the less as possible allowing free parts so that the rockplaster retains the metallic parts before making nests, after the curing the coating will be removed easily by brushing with water. An example of a conventional dental coating which may be used is Cristobalite which comprises quartz or silicate powder with plaster. The techniques are:

1) For the acrylic crowns: the coating has to be put inside or through the hollow and some of it through lingual or palatine border. (FIG. 5.12). If there is an acrylic crown with pins, the coating has to cover alongside the pin and also by the lingual or palatine part without touching the white wax. (FIG. 6.12).

2) For the pivots: coating has to be placed alongside the pin without touching the white wax. (FIG. 7.12).

3) For the inlays or pillars of a metal bridge, all the metallic parts have to be covered without touching the white wax with or without plastic mask. (FIG. 8.12).

DENTAL TECHNIQUE OF THE HORIZONTAL AND VERTICAL NESTS:

They are called horizontal nests because of the position and the placement of the wax pattern (lain), (FIG. 9*a*) we let the vestibular, lingual or palatine face uncovered to be filled by dripping of the fluid heatcuring acrylic. (FIG. 9.24)

They correspond for the finishing of:

1-Jackets.
2-Pivots.
3-Veeners of the acrylic crowns.
4-Plastic mask of the fixed metal bridges.
5-Heatcuring acrylic fixed bridges.

TECHNIQUE:

The horizontal nests are as some flat cookies made of rockplaster that measure about 2 cm of large and width by 1 cm of height (FIG. 9*a*) for a jacket of normal size, to make them about 10 gr. of rockplasterare needed.

A mixture creamy rockplaster is prepared, cast inside the jacket, or of the acrylic crown, through the borders of the pivot until it covers the wax borders. The rest is capsized on a flat surface (without vaseline it) so that the white wax pattern with or without plastic mask be introduced through the center of the nest in lain position, and covering all the vestibular, lingual or palatine face; the occlusal faces and the approximal contact points, letting an uncovered face (that can be vestibular, lingual or palatine) to be filled by dripping of the fluid heatcurable acrylic. If the white wax pattern have not a plastic mask, that is, it has a molded vestibular white wax whose palatine wall can have occlusion marks or hooks marks of a partial prosthesis, an horizontal nest is made leaving the uncovered vestibular face for the filling by dripping of fluid heatcurable acrylic. (FIG. 9.24) In the horizontal nests the internal wall is used to retain the plastic mask (FIG. 10.9) or to maintain the form of the tooth made in white wax either by the lingual- palatine or vestibular side that has the mark of a hook of a partial prosthesis. (FIG. 11.16) Leaving an uncovered face for the filling by dripping of fluid heatcurable acrylic. (FIGS. 9*a*, *d*.24; 10.24; 11.24; 12*a*, *b*.24; 13 to, *b*, *c*, *d*, and, *f* and *g*.24)

When the rockplaster of the horizontal nest covers the occlusal face, it is a horizontal nest with occlusal coating. (FIGS. 12*a* and *b*.17).

If it does not have occlusal coating is a horizontal nest without it (FIGS. 9*a* and *b*.18) because it has a rockplaster lid that serves to maintain the plastic mask, marks of the hooks, dental morphology and vertical dimension, that is called Retainer.

The retainer can be half-retainer or entire retainer, farther on we will detail the technical part. There are two techniques to make horizontal nests:

1) The horizontal nests without occlusal coating correspond to the FIGS.: 9*a*, *b*, *c* and *d*.18; 13*a* to *g*.18. The half retainers are those which cover the upper face of the horizontal nests without occlusal coating and correspond to the FIGS.: 9*d*.20; 13*a*, *b* & *c*.20; 20*a* & *b*.20. The entire retainers that cover over the upper face of the horizontal nests without occlusal coating correspond to the FIGS.: 9*c*.23; 13*d*, *e*, *f* and *g*.23; and 21*a* & *b*.23.

2) The horizontal nests with occlusal coating are shown in the FIGS.: 11.17; and 12*a* & *b*.17. Entire retainers are not used on the horizontal or vertical nests with occlusal coating. Another technique consists of duplicating the model to make the horizontal nest according to the required work, therefore they are called duplicated horizontal nest.

TECHNIQUE ON THE DUPLICATED HORIZONTAL NESTS:

Having an acrylic crown with pin or a cantilever bridge, both works can be with or without plastic mask, the model is duplicated using alginate to make a new model in rockplaster, (the pillars or the metallic part shoulds be covered with coating as was explained previously).

Once the rockplaster has hardened, the model of the impression is removed, the excesses of plaster are trimmed and a horizontal nest without occlusal coating is made, leaving the uncovered vestibular face for the filling by dripping of fluid heatcurable acrylic; if it is wished to preserve the vestibular face, a half or entire retainer has to be placed leaving uncovered a third of the face for the filling by dripping of fluid heatcurable acrylic.

2o) Now we will detail the differences on the vertical nests in comparison with the previous nests. The vertical nests are high cookies, almost cylindrical due to the position in which is located the wax pattern in vertical position and are of 2,5 cm high and 1.5 cm in diameter.

They correpond for the finishing of:
1-Pivots.
2-Acrylic crowns.
3-Venners of the fixed bridges.
4-Heatcurable acrylic fixed bridges.

There are two techniques to make vertical nests:
1) Entire vertical Nest could be with or without half retainer. (FIGS. 14 and 15)
2) Half vertical Nest could be with or without entire retainer. (FIGS. 16a, b and c.22)–(FIGS. 17a and b.22). The vertical nests do not have occlusal coating. To make the entire vertical nest for a pivot with or without plastic mask of normal size about 12 grs. of the rockplaster are required.

TECHNIQUE:

Fill with creamy rockplaster on the gingival rim. With the rest of the rockplaster is capsized, making a nest in cylindrical form, the pivot with or without plastic mask with the gingival rim downward, is introduced through the center of the nest (FIG. 14.21), and the faces are covered: vestibular, by the approximal sides (contact points), by lingual or palatine, leaving uncovered one third of the incisal or occlusal face. These are "the entire vertical nests without occlusal coating" (FIG. 14.24) which allow us to make opaque the metallic stump part of the pivot by occlusal. This uncovered occlusal face is for the filling by dripping of fluid heatcurable acrylic. (FIG. 15.24) and it may have or have not half retainer.

These are entire vertical nests with half-retainer (FIG. 15.20). To substitute a plastic mask in white wax of a fixed metal bridge by heatcurable acrylic a half vertical nest has to be made because we let two uncovered faces:
1) One by vestibular. (FIGS. 16 to, c.9.24).
2) Other by palatine or lingual. (FIGS. 16b, c.24)
1) If the acrylic crown does not have vestibular plastic mask, or we have to pigment a special zone the uncovered face has to be the vestibular. A rockplaster wall has to be made by lingual or palatine (FIG. 17a.44). The filling by dripping of heatcurable acrylic will be made through vestibular, and after the curing is finished by giving the vestibular dental form.
2) In the vestibular face a vestibular entire retainer will be put, the uncovered face has to be by lingual or palatine for the filling by dripping of the fluid heatcurable acrylic and after it is cured it is finished by giving the lingual or palatine dental form. Later on, we will explaine in detail the techniques on the half and entire retainers.

An entire retainer is used by vestibular to separate the vestibular face of the vertical nest to make opaque the metallic part of the pivot, then it is put back in its original position for the filling by lingual or palatine with the dripping fluid heatcurable acrylic, (FIGS. 17a, b.24).

The half retainer are placed on the occlusal face of the vertical nests without occlusal coating. (FIG. 15.20)

The entire retainers are put on the vestibular face of the vertical nest without occlusal coating (FIGS. 17a, b; and 19a, b).

These are called vertical nest duplicates, and are those that duplicate the main model for the finishing of the requested work.

THE VERTICAL DUPLICATES NESTS:

There are called vertical nest duplicates those to which the main model is duplicated with alginate to make a new rockplaster model of the die with the white wax to preserve the original die-model. (FIG. 18).

For example: on two separate acrylic crowns but, neighboring mutually and that can not be worked together, because the heatcurable acrylic flows through one veneer, but leaves the place and continues flowing through the other veneer, (FIG. 18). After the boiling, in the elimination of the jointed veneers of the nest, it is impossible to separate the half-acrylic parts, and the approximal contact points and the vestibular mesials forms will be lost.

TECHNIQUE:

Having two central tooth made on acrylic crowns with the veneers in white wax we have to take an impression in alginate on the original model and once the moulding compound has hardened, remove the impression from the original model with the crowns.

Without making the casting, one of the crowns of the impression has to be removed, to make the casting of one of these crowns with rockplaster and let the rockplaster harden. The impression from the model is removed and the other is placed back in the corresponding place and another model in rockplaster is made and hardened. The impression is removed and we have two models with two separate central crowns. The two veneers are washed with hot water to eliminate completely the white wax and paintbrush with opaquer on the metalic parts. (FIGS. 19a and b.). It is allows to dry and the fluid heatcurable acrylic with the color of dentine is filled by dripping on one acrylic crown, and then on the other. Both models have to rest on a plain element so that the heatcurable acrylic does not overflow the place. The heatcuring acrylic is prepared again for pigmenting the neck of the two acrylic crowns. The acrylic is filled immediately on the gingival zone of the necks and is allows to forge for a while.

The heatcurable acrylic of incisal tone/color is prepared and the complete vestibular face of each acrylic crown is immediately filled with it. Once the heatcurable acrylic has lost the sheen, immediately set to curing.

On this way the two acrylic crowns will have the same tone and the same thickness of the vestibular acrylic by having as reference the neighboring acrylic crowns. After the curing and the elimination of the vertical duplicates nests, these acrylic crowns are put on the original model-die to be finished by giving them the final form and polishing.

If there will be acrylic crowns with plastic mask and wax, vertical duplicates nests with entire retainer are made leaving uncovered a third of the vestibular face in order to receive the filling by dripping of fluid heatcuring acrylic that it will be by mesial-distal. (FIGS. 19a, b.24) The white wax are eliminated, and it is filled with the heatcurable acrylic by the mesial-distal side, and once the heatcurable acrylic has lost the sheen, it is cured, cooled, and the retainers and the acrylic crowns of the duplicated models are eliminated to put them on the original models to file and polish them.

For fixed metal bridges without plastic mask a half vertical duplicate nest has to be made placing a wall by lingual or palatine (FIG. 17.44) In the event that plastic mask will be put, vestibular entire retainer will be placed and the heatcurable acrylic will be filled by lingual or palatine. (FIG. 17a without the wall 44).

DUPLICATED NESTS TO COPY THE FORMS OF NATURAL TEETH BEFORE THEIR EXTRACTION, IN ORDER TO HAVE A REPLACEMENT TEETH SET, WITH JACKETES OR HEATCURABLE ACRYLIC BRIDGES

Before extracting the natural teeth the dentist takes two impressions with alginate on the natural teeth of the patient. Once the impressions are ready, they are casted with rockplaster to obtain the original model.

The other impression is casted with melted white wax to obtain the forms. Once the waxhas hardened, it is removed from the impression and horizontal or vertical multiple nest is made to substitute in heatcurable acrylic.

Once the jackets or bridges are cured, we can use these to substitute a jacket, a pivot or a heatcurable acrylic fixed bridge with the forms of the natural teeth that had the patient.

THE MIXED NESTS:

There are called mixed nests the simultaneous combination of the vertical and horizontal nests that are used for the finishing of fixed metal bridges, as the pieces employed for these allows us to finish with heatcurable acrylic on one nest.

MARKS OF THE NESTS.

The nest has to be marked scraping with the edge of a spatula on the side of the retainer or of the wax pattern indicating:

The color of the acrylic, (in order not be confused when there are several works),where the gingival and oclusal zones are located. More than ten nests, which can be placed inside a curing container and within the processor apparatus. Until a maximum of three curing containers at the same time to make the boiling, during that boiling there will not be variations or pigmentations between the nests that may affect the curing of the pieces.

RETAINERS:
1) half retainer.
2) entire retainer.

The horizontal or vertical nests (the white wax made with or without plastic mask) can have or have not PLASTER RETAINERS. The retainers are like lids or rockplaster counterparts, that are joined on the uncovered face of the horizontal or vertical nests without occlusal coating and they can have two forms:
1) one of them is the half retainer:
a) the one which conserves the form of the occlusal face of the tooth.
b) the one that at the same time maintains the vertical dimension of the incisives and molar teeth.
c) It also is the one that maintains the marks of the hooks. See on (FIG. 9d.20 FIGS. 13a, b c.20 and FIGS. 20a and b.20)

The uncovered face is for the filling by dripping of the fluid heatcurable acrylic.

2) the other one is an entire retainer that can have two forms:
1) The entire retainer with one third of uncovered face to be filled by dripping of heatcurable acrylic and it has be by distal and mesial. (FIG. 9c.24, FIGS. 13d to g.24, FIGS. 19a, b.24)
2) The other one, can have an entire retainer without letting one third of uncovered face for the filling by dripping of fluid heatcurable acrylic, which has to be by lingual or palatine.(FIGS. 17a and b.) and it is:
a) the one which grasps the vestibular plastic mask of the wax pattern during the elimination of the white wax by washing with hot water, and when receives the fluid heatcurable acrylic until finishing the curing.
b) the one which conserves the vestibular face made in white wax prepared with the dental morphology, without varying the thickness of the heatcuring acrylic.
c) the one which conserves the marks of a vestibular hook of a partial denture. (FIG. 13d.) Both half and entire retainers are made on the horizontal and vertical nests without occlusal coating.

TECHNIQUE OF THE RETAINERS

Before making the retainers we have to study which are the zones of white wax of the dental structure that can not be modified to place these retainers. The retainers can be individual for making only one work, or multiple for making several pieces as for example a fixed bridge of several pieces. In some special cases on the same nest can be half and entire retainer; these are called combined retainers.
1) HALF RETAINER (the uncovered face is for the filling by dripping of fluid heatcurable acrylic by lingual, palatine or vestibular sides.)

A horizontal nest without occlusal coating is made, introducing the wax pattern toward the interior of the nest leaving one uncovered face. (FIGS. 9a,b,c .15)—If the wax pattern has a plastic mask, it has to be placed on the opposite side, letting the lingual or palatine face uncovered. (FIGS. 13a, b. 15) until the nest has hardened.

On the gingival zone of the uncovered face of the horizontal nest a small undermined is made without injuring the white wax pattern. (FIG. 20a. 30). The vestibular zone from the mesial to the distal sides and the small undermined are vaselined, and the rockplaster is prepared to cover by the vestibular zone leaving uncovered the incisal face. The half retainer has to have two millimeters of thickness, and rockplaster is used for its resistance.

To let the lingual or palatine face uncovered of the wax patterns with or without a plastic mask to those which should not touch the marks of the occlusion or of the hooks should accomplish horizontal nests without occlusal coating with half retainer. (FIGS. 13a, b and c.20). The filling it by dripping of heatcurable acrylic will be through the middle of the tooth from under occlusal face toward gingival, or from the incisal border to the middle of the tooth.
2) ENTIRE RETAINER: (the uncovered face for the filling by dripping of the heatcurable acrylic is by lingual, palatine, distal and mesial sides.) Having the horizontal or vertical middle nest without occlusal coating with the uncovered face, (with or without plastic mask), it is undermined as it is explained above and drawn on (FIG. 20a.30) and the vestibular face is vaselined all over. Rockplaster is prepared, and all the vestibular face is covered on the uncovered face of the horizontal or vertical middle nest beyond the wax edges of the wax pattern. (more than 3 mm). The entire retainer is filled without leaving one third of uncovered face because the fluid heatcurable acrylic will fill by lingual or palatine. (FIGS. 17a, b.24 .44)

If the heatcurable acrylic will fill by vestibular it has to be made an entire retainer with one third of uncovered face by the mesial or the distal side for the horizontal nest, (FIG. 9c.23; FIGS. 13d, e, f, g.23; FIGS. 19a, b.23 and FIGS. 21.a, b.23); for the middle vertical nest make an entire retainer by vestibular with one third of uncovered face by lingual or palatine a wall of rockplaster is placed in order to avoid theat the fluid heatcurable acrylic overflows.

The entire retainer has to have approximately three thickness millimeters, and rockplaster has to be used. If it needs more than three mm. it has to be made of Paris plaster or Stone plaster and after the curing it has to be removed from the nest easily as they are not resistent.

TECHNIQUE FOR WETTING THE NESTS WITH OR WITHOUT PLASTIC MASK WITH OR WITHOUT RETAINERS.

Before eliminating the wax patterns it is always necessary to wet the nest with or without retainers for three minutes. It is enough to submerge them in water at room temperature and then make the washing with boiling water. It is necessary to wet the nests so that the rockplaster remains wet avoiding the use of isolators.

TECHNIQUE TO REMOVE THE WHITE WAX OF THE NESTS

To eliminate the white wax it is necessary to wash with hot water, pouring on the nest to soften the white wax, and then the nest has to be turned around to change the position of the spurt of hot water so as to facilitate the removal of any rests of white wax. Before eliminating more white wax (FIG. 22) it is necessary to eliminate the excesses of rockplaster (around the contours of the hollow for the filling by dripping of the fluid heatcurable acrylic).

Then it is trimmed with a scalpel, compressed air is passed to clean and the washing continues until all the wax and rockplaster are completely eliminated.

If excess of plaster is not eliminated, the plaster will mix with the fluid heatcurable acrylic, and after the boiling, the plaster mixed with the acrylic have to be eliminated and it will be necessary to add more heatcurable acrylic, to cure and finish (without making nests). If there are retainers, they are lifted outward with the aid of a knife to continue washing until they are completely clean and separated (the nests and retainers.)

TECHNIQUE TO ELIMINATE THE WATER DEPOSITED INSIDE THE NESTS, OR FROM THE RETAINERS WITH OR WITHOUT PLASTIC MASKS:

A jet of compressed air is passed to eliminate the deposited water inside the nest. In the case that the water were not eliminated, then the cured heatcurable acrylic will be porous having bubbles inside it, because it is mixed with water.

When the nest and the retainers are wet but not flooded with water, they are paintbrushed with the opaquer on the metallic part of the acrylic crowns or of the pivots, and all the pontic faces of the fixed metal bridges.

TECHNIQUE FOR JOINING THE RETAINERS WITH THE HORIZONTAL AND VERTICAL NESTS:

The horizontal and/or vertical nests and retainers have to be already separated and clean. By the internal side of the half retainer we see the dental structure form, the occlusal anatomy and the marks of the hooks of a dental prosthesis.

In the internal part of the entire retainer we see that the plastic mask was housed, or the form of the dental structure and also the marks of the hooks of the dental prosthesis. The internal parts of the retainers (half or entire) have to coincide and join on the vestibular face of the nest (horizontal or vertical). Once they are joined, the joint has to be fixed with a quick cement or Paris plaster far from the hollows in wich the filling of the fluid heatcurable acrylic will be made.

TECHNIQUE TO POLYMERIZATION OF THE HEATCURABLE ACRYLIC:

Before making the works it is necessary to know about the polymerization of the HEATCURING ACRYLIC for our method:

The white heatcuring acrylic fulfils 4 stages of polymerization:

1') FLUID.
2') FIBROUS.
3') ELASTIC.
4') DOUGHY.

1' Stage: When powder and monomer are mixed without allowing them to rest; that is the FLUID stage. (Is semi-liquid). Immediately it is necessary to fill on the hollows of the nests. The filling is made by dripping with the aid of a canoe shaped spatula through which it flows, using together the vibrator to complete the casting.

2' Stage: After, the fluid mixture is allowed to rest until a FIBROUS paste is formed which is to be mixed with a color to pigment, any required zone.

3' Stage: The ELASTIC mixture, this is the stage in which it is able to rebase or adapt a border.

4' Stage: DOUGHY is the final stage of the polymerization, to turn this mixture back to the ELASTIC stage in order to be able to work it again it is necessary to add a drop of heatcurable monomer. When the heatcurable acrylic passes through these stages without making the boiling, it is not cured; when the boiling is made with the processor apparatus during 15 minutes, then it will be completely polymerized remaining cured and hard.

TECHNICAL OF PREPARATION:
1) TO FILL WITH HEATCURING ACRYLIC
2) TO MAKE THE BOILING.
3) THE INSTANT COOLING.
4) TO ELIMINATE THE WORK FROM THE NEST.

With the nests made, the heatcurable acrylic is worked in the flowing form OF THE FIRST STAGE which is filled by dripping in the hollows of the nests.

The portion of the white heatcuring powder necessary for a jacket with or without plastic mask is about 0,4 gr. and the heatcuring monomer to mix with the powder needed some 0,2 grams (approximate weights).

If there are many pieces, the heatcurable powder and monomer are added in the same proportion for each piece. A small portion of the white heatcurable powder is placed in a glass hollow pot, then the heatcurable monomer is added to be mixed it with the aid of a spatula to form a semi-liquid mixture, it is stired very well. In the event that it were a little thick a drop of heatcurable monomer has to be added and mix again until it gets semi-liquid and light.

Before filling with the mixed heatcurable acrylic through the hollow of the nest it is necessary to add a drop of heatcurable monomer drop on the rockplaster stump in order to be absorbed so that when it receives the fluid heatcurable acrylic it will complement the wanting liquid. It is not necessary to put a heatcurable monomer drop on the metallic part with opaquer (on the veneers of the acrylic crowns, the pivots and the fixed metal bridges).

The nest has to be sustained with the hollow upward over the vibrator in motion, then it is filled with the fluid heatcurable acrylic by the DRIPPING FORM WITH THE AID OF A SPATULA (canoe shaped) (FIG. 23.29) it has to be filled on one side so that by the opposite side overflows out until covering the rockplaster stump or other work to allow the air bubbles to leave (FIG. 24) and when continue adding until is filled completely. (FIG. 25c.36) To eliminate the air bubbles, it is enough to remove the heatcurable acrylic with the top of a pin without injuring the rockplaster and allowing to vibrate for a while (has to be removed the acrylic when it is fluid).

The nest is removed from the vibrator and it is allowed to rest on a smooth surface or is leant to a vertical element so that the heatcuring acrylic does not overflow its place.

The remaining mixture is lid with a paper napkin; after the curing, the remaining piece of this mixture can be use again to rebased some lacking border of the piece or to mix with other color to adapt on the cured acrylic part; also another work can be repaired with the same tone, or it is prepared for pigmenting. To mix the colors it is always necessary to add more heatcurable monomer, make splits, calcium or fissure marks with the remanent of the same mixture. During the rest of the nest, if we see that the heatcuring acrylic sanks in the surface (FIGS. 25a, b) it is necessary to add a heatcurable liquid drop (FIG. 25b.37) on the hollow filling with more fluid heatcurable acrylic; the fluid heatcurable acrylic is prepared again to fill on the sunk acrylic until it is full (FIG. 25c.36); the remaining heatcurable acrylic will serve us to amend the details or pigment.

After the rest, it is necessary to verify that the heatcurable acrylic is on the level (FIGS. 25c and 26.36) and is allowed to pass to the fourth stage of polymerization, once it is hardened it has to be put inside of a curing container that contains running water, immediately it is submerged inside the processor apparatus heated at 90° C., close the processor with the main lid, inject compressed air up to a pressure of 3.5 bars and cure for 15 minutes.

The normal boiling takes 15 minutes for a thickness of heatcuring acrylic of approximate 2 to 3 mm. (jackets, rebased, veneers, pivots and bridges). For the repairings, or the small rebased, or to pigment, put a calcium point, make clear or darken the color in a thinner place, the boiling takes 5 minutes.

After the boiling the processor apparatus has to be swiched off (it is convenient to swich off the processor 5 minutes before ending the time of the boiling.) After this time, eliminate the air from the processor apparatus until the gauge shows 0 pressure bar, open the main lid and removed the curing containers from the processor. The cooling of the curing containers with the nests, is immediate, the nests being maintained inside the container are cooled with the jet of water tap until the water of the curing container is cold.

The works are removed from the nests with the aid of a scalpel pressing the retainer to break it in small pieces, once the retainer has been removed the breaking of the plaster continues until the work is release, it is washed with soap and water. It is always necessary to remove the works immediately after the boiling because the plaster crumbles due to the pressure. If it is not eliminated it has to be let soaking in water to eliminate it in another time. If it is not let soaking the plaster will be dry and stay hard.

After the work has been separated from the nest or from the model, the excess of acrylic is filed and the work is placed on the original model to verify the borders. If it is desired to color any zone, this zone is filed and a drop of heatcurable liquid is added, then a drop of fluid heatcurable acrylic (recently made) is put on, and it is immediately submerged in water at room temperature in the curing container with or without the die or nest to cure for five minutes, at working pressure; afterwards, it is removed from the processor apparatus to cool it and it is filed to finish and polishing.

If, there is not any hurry, it can be let to rest until is cooled at room temperature. It can be let all the time wished soaking in water up to several months, because the rockplaster conserves itself wet to make ease its expelling of the nest. Once the work is removed from the nests, it is ready to file and polish.

THERE ARE THREE WORKING FORMS WITH HEATCURABLE ACRYLIC WITHOUT CURING IT, BY:
1) Indirect method:
2) Direct method:
3) Adaptation.

1) Indirect method: it is the method of the dental technician that prepares the fluid heatcurable acrylic and is filled by dripping in the hollows of the nest and the boiling is made immediately.

2) Direct method: the odontologist prepares the heatcuring acrylic, it is allowed to pass the elastic stage, rebased it in mouth, then it is removed and submerged inside of a glass pot with running water to send to the laboratory, to make the final boiling and to polish it.

3) Adaptation: the dental technician prepares the heatcurable acrylic and allows to harden until its being between the doughy and elastic stages. It is ideal to adapt the work on the definitive die and it is cured with or without the die.

TECHNIQUE FOR:
1) REBASING.
2) PIGMENTING.
3) FISSURES OR SPLITS MAKING.
4) CALCIUM POINT.
5) THE FISSURES OF JACKETS OR ACRYLIC BRIDGES REPAIRING.

1) TECHNIQUE OF THE METHODS FOR REBASING WITH THE HEATCURABLE ACRYLIC:
1) DIRECT METHOD.
2) INDIRECT METHOD.

By the direct method the rebasing made with the heatcurable acrylic in the mouth (done by the dentist) when lacks a border of a jacket, a veneer or a pivot, and the borders of the pontic because the gum has withdrawn, when it is corrected in this form it is avoided taking new impressions and the waste of consults. The technique is very simple, the heatcurable acrylic is prepared, is allowed to hardened until the elastic stage with the dry, clean spatulas, it is kneaded and a drop of heatcurable liquid on the zone to be rebased is added, with the rest of the elastic heatcurable acrylic is put on it is pressed and is carried to the place.

The heatcurable acrylic is placed on the edge and it is pressed and is taken to the place to verify if it adapts well to the edges, and it is removed with care. It is immediately submerged in a small glass bottle with running water and is close to send it to the laboratory to make the boiling.

By the indirect method, the elastic acrylic part is rebased on the definitive die, it is put on the curing container to make the boiling with or without the die. The boiling is always made with the processor during 15 minutes, and then it is removed from this to cool with running water to file and finish the polishing.

2) TECHNIQUE OF PIGMENTING:

NECKS: the zone to pigment is filed, to deepened slightly with a round mill, and the powder is eliminated. If it is necessary to add a drop of heatcurable liquid on this zone. The fluid heatcurable acrylic is prepared with the aid of a spatula, then a portion of acrylic is taken and a drop is allowed to fall in the hollow without surpassing the filed zone, then it is waited until loses the sheen, and it is immediately submerged in the curing container (without the die) to cure for five to ten minutes, then it is removed from the processor, is cooled, is filed and polished.

DENTINE: In the vestibular face, a part of the cured heatcurable acrylic is removed to add the pigment of dentine to make it clear or darken it according to the case. A drop of heatcurable liquid is added on the filed zone and a part of pigmented fluid heatcurable acrylic is put on the vestibular face until it loses the sheen; then immediately it is put to cure for five to ten minutes, and it is removed from the processor apparatus, it is cooled, filed and polished.

3) TECHNIQUE FOR MAKING FISSURES OR SPLITS.

A rut has to be carved in the vestibular face, the powder of the carving having to be removed, then a drop of liquid is poured and a small portion of heatcurable acrylic is placed on the fissure, and wait until loosed the sheen.

Immediately it is submerged inside of the curing container, to cure for five to ten minutes, then it is removed from the processor, is cooled, is filed and polished.

4) TECHNIQUE OF MAKING CALCIUM SPOTS:

The vestibular face is drilled, and worked in the same form as for the fissures or splits.

5) TO REPAIR FISSURES OF JACKETS OR HEATCURING ACRYLIC BRIDGES:

It is used the indirect method and the following steps:

The dentist puts on the mouth the fissured jacket (it is fissured due to an accident or due to the selective grinding) and reduces the stump to give it more thickness for the new refilling of heatcurable acrylic he glues it with blue wax, take an impression with alginate and removed both (impression with the jacket or acrylic bridges within) to send them to the dental laboratory.

The dental technician makes the cast with rockplaster to make a new model. Once this has hardened, the impression is removed from the model, and we see the jacket that remains adhered to the model and it is glued with blue wax; the blue wax indicating us that this is the fissured zone.

The model has to be soaked for five minutes to wet it, the blue wax is eliminated with hot water. Only the zones to be repaired is filed, the fluid heatcurable acrylic is prepared, a drop of heatcurable monomer is poured in the fissure until covering it completely and then it is cured for 15 minutes. (with the model submerged inside of the processor). After the boiling the work is removed from the processor apparatus, it is cooled with running water, and the jacket is removed from the model to file and polish.

DENTAL TECHNIQUES ON THE WORKS TO SUBSTITUTE IN HEATCURING ACRYLIC WHICH ARE WRITTEN IN THE FIRST PAGE:

The casting of the fluid heatcurable acrylic (first polimerization stage) that will be filled by dripping in a prepared hollow of the nests is used in the following works:

1) THE JACKET MADE IN WHITE WAX WITHOUT A PLASTIC MASK is made of a horizontal nest without occlusal coating and a hollow is prepared for the filling by dripping of fluid heatcurable acrylic that can be:

a) by vestibular side.

b) by lingual or palatine side.

a) THE FILLING BY DRIPPING IS BY VESTIBULAR:

The horizontal nest without occlusal coating with the vestibular face uncovered is made for the filling by dripping of fluid heatcurable acrylic due that the lingual or palatine faces are previously marked to be the pillars of the hooks of a dental prosthesis. The uncovered vestibular face is also used to pigment or mix one or more colors. After the curing, it is finished by giving the form to the vestibular face. (9a.18)

b) THE FILLING BY DRIPPING OF HEATCURABLE ACRYLIC IS BY LINGUAL OR PALATINE:

A horizontal nest without occlusal coating is made leaving uncovered the lingual or palatine face for the filling by dripping of heatcurable acrylic; once the curing it is finished giving the form with the help of the occlusor or of the neighboring teeth as the vestibular face is marked by a hook of a dental prosthesis or to not modify the anatomy of that vestibular face. (FIG. 10).

2) THE JACKET MADE IN WHITE WAX WITHOUT A PLASTIC MASK AND WITH RETAINER:

The jacket made in white wax that it is pillar of a hook of a dental prosthesis has marks of the hook by vestibular, lingual or palatine, it has to be made a horizontal nest without occlusal coating and half retainer that covers lingual or palatine and occlusal face, in addition to the marks of the hook of the dental prosthesis (FIGS. 13a, b and c.16) leaving uncovered half lingual or palatine as a hollow for the filling by dripping of heat curable acrylic. After the curing the excesses of acrylic are filed, and it is polished. If an entire retainer is put, the distal or mesial face is left uncovered for the filling by dripping of fluid heat curable acrylic. (FIGS. 13d to g.24).

3) JACKET MADE IN WHITE WAX WITH A PLASTIC MASK:

The plastic mask has to have grip of selfcuring acrylic. A horizontal nest with occlusal coating is made. The filling by dripping of fluid heat curable acrylic is by lingual or palatine, as the plastic mask is included in the nest. (FIGS. 11 and 12.17). After the curing and the elimination of the nest, the grip and the excess of acrylic are filed, and the occlusion is controlled with the aid of an occlusor. Then the anatomy is given in order to finish the polishing.

4) THE JACKET MADE IN WHITE WAX WITH PLASTIC MASK AND WITH RETAINER:

The horizontal nest without the occlusal coating is made, and it is worked in the same form as explained in paragraph no2. (FIGS. 13.a, b and c.18)

ANOTHER TECHNIQUE: Having a jacket made in white wax with a plastic mask with grip with or without hook marks by lingual or palatine, a horizontal nest without occlusal coating is made leaving uncovered all the vestibular face of the plastic mask and one approximal contact point. The vestibular face of the horizontal nest without occlusal coating is vaselined without passing it on the plastic mask, in order to make an entire retainer, leaving uncovered a third of face at one side of the contact point which can be by distal or mesial that will be the hollow for the filling by dripping of the fluid heatcurable acrylic. (FIGS. 13f and g.24).

When the white wax is eliminated, we see the plastic mask which will be housed in the internal part of the entire retainer. Once it is clean, both (nest and retainer) they will have to be glued with a drop of cianoacrilate or with plaster of Paris without touching the approximal hollow. The dripping of the fluid heatcurable acrylic will fill through this hollow, when it is hard, cured, it is removed from the processor apparatus to cool, and the work is removed from the curing container and from the nest and is finished giving the form of the approximal contact point and then it is polished.

IMPORTANT NOTICE: When a (horizontal or vertical) nest without occlusal coating with retainer (half or entire) is made, it is necessary to leave well uncovered all the vestibular side of a plastic mask (with grip) or the retainer will not got out of the nest, or the plastic mask will not be able to house in the interior of the retainer.

5) THE PIVOT MADE IN WHITE WAX WITHOUT PLASTIC MASK.

There are made two nests:

1) horizontal.

2) vertical.

1) HORIZONTAL NEST:

FILLING BY DRIPPING IS BY VESTIBULAR, because it has linguals or palatines marks of a hook of a dental prosthesis. To opaquer and pigment the metallic part (stump) of the vestibular zone it is necessary to make a horizontal nest, without occlusal coating. All the vestibular face has to be left uncovered to make the filling by dripping of the fluid heatcurable acrylic and after it is cured, it is finished giving it the form of the vestibular tooth (FIG. 27.24).

2) VERTICAL NEST:

THE FILLING BY DRIPPING IS BY OCCLUSAL; Because it has marks of the hooks of a dental prosthesis by lingual, palatine and vestibular. It is necessary to make an entire vertical nest without occlusal coating.

When the white wax is eliminated we can opaque the vestibular and lingual or palatine part. The fluid heatcuring acrylic will fill by occlusal (FIGS. 14.24 and 15.24.) After the curing it is finished giving the occlusal anatomy.

6) THE PIVOT MADE OF WHITE WAX WITHOUT PLASTIC MASK AND WITH RETAINER.

It is made with the techniques explained in the paragraphs: n'5 for the realization of the horizontal nest and n'2 of the form how the half retainer is employed.

7) THE PIVOT MADE OF WHITE WAX WITH PLASTIC MASK:

The pivot with plastic mask with selfcuring acrylic grip, make a vertical nest without occlusal coating, leaving free the occlusal face to opaque and also to make the filling by dripping of the heatcurable acrylic. After it is cured, the grip and the excess of the heatcuring acrylic are eliminated to give the form of the occlusal face. (FIG. 14.24)

8) THE PIVOT MADE OF WHITE WAX WITH PLASTIC MASK AND WITH RETAINER.

It has to be done in two forms:

1) The pivot with plastic mask with grip of selfcuring acrylic, a horizontal nest without occlusal coating with entire retainer will be made leaving a third of uncovered face by distal, mesial or occlusal for the filling by dripping of fluid heatcurable acrylic. (FIGS. 13.*d.* and *e*.24 and FIGS. 21.*a* and *b*.24)

After it is cured, it is finished giving the occlusal, distal or mesial form.

2) The pivot with plastic mask with grip, an entire vertical nest without occlusal coating with half retainer is made. (FIG. 15.20) and the filling by dripping of fluid heatcuring acrylic will be by occlusal, and after it is cured it is finished giving the occlusal form.

9) THE ACRYLIC BRIDGE MADE OF WHITE WAX.

A multiple vertical nest with occlusal coating (FIG. 28.39) is made leaving uncovered the lingual or palatine faces to be filling by dripping of fluid heatcurable acrylic. (FIG. 28.24).

The white wax is eliminated and it is filling by dripping of fluid heatcurable acrylic by the lingual or palatine zones.

After the curing, the heatcuring acrylic excesses are eliminated to make the final polishing.

10) THE ACRYLIC BRIDGE MADE OF WHITE WAX WITH INTERNAL REINFORCEMENT.

It is employed the same technique of the paragraph No.9, with the previous aggregate of a reinforcement of stainless steel wire glueing it with selfcuring acrylic of the same color of the heatcuring acrylic, from the first pillar to the last pillar before filling by dripping with fluid heatcuring acrylic.(FIG. 29 41).

11) THE ACRYLIC BRIDGE MADE OF WHITE WAX WITH PLASTIC MASK.

The plastic mask of the bridge has to have individual grips for each plastic mask, then the same technique of the paragraph No. 9. is followed See FIG. 30*a* (bridge of the anterior lower incisives), FIG. 30*b* (of the posteriors either upper or lower pieces) and FIG. 30*c* (of the anterior upper incisive.)

12) THE ACRYLIC BRIDGE MADE OF WHITE WAX WITH PLASTIC MASK WITH INTERNAL REINFORCEMENT.

There are employed the techniques of the paragraphs Nos. 9, 10 and 11.

THE VENEERS:

13) OF THE ACRYLIC CROWN MADE OF WHITE WAX.

A horizontal nest without occlusal coating is made covering all the metallic faces leaving uncovered only the vestibular face to opaque and to be filled by dripping of fluid heatcurable acrylic as shown in the FIG. 13*a*.18 on the horizontal nest without occlusal coating.

The white wax is eliminated and then the filling with fluid heatcurable acrylic by dripping is made as shown in the FIG. 23.37. After it is cured, it is finished giving the form to the veneer and it is polished.

14) OF THE ACRYLIC CROWN MADE OF WHITE WAX AND WITH RETAINER.

To make an acrylic crown with a veneer in molded white wax, it has to be done a horizontal or vertical nest without occlusal coating with half or entire retainer to maintain the dental form and to opaque the vestibular face. Both retainers have to have uncovereda third of face for the filling by dripping of fluid heatcurable acrylic which will be by distal or mesial and that after the curing it is finished by giving the form.

15) OF THE ACRYLIC CROWN MADE OF WHITE WAX WITH PLASTIC MASK AND WITH RETAINER.

The method is the one to make a horizontal or vertical nest without occlusal coating with half or entire retainer for the plastic mask with grip of selfcurable acrylic, leaving uncovered a third of face and then the technique of the paragraph No. 14. is followed.

16) THE FIXED METAL BRIDGE MADE OF WHITE WAX.

The pillars of the metal bridge have to be covered with coating, the gingival and lingual or palatine edges of the pontic have to be covered with rockplaster (FIG. 31.43) to make a horizontal nest without occlusal coating leaving uncovered the vestibular face and a plaster wall has to be made by lingual or palatine of the pontic. The uncovered vestibular face is for the filling by dripping of fluid heatcurable acrylic which it is only by vestibular, the plaster wall serves to retain the exit of fluid heatcurable acrylic by this side. After it is cured, it is filed to give the form of vestibular tooth and to polish it.

17) THE FIXED METAL BRIDGE MADE OF WHITE WAX AND WITH THE RETAINER.

For aesthetic reasons of the pontic and in order not to modify its form is it necessary to make a horizontal nest without occlusal coating with an entire retainer leaving uncovered only a third of face which can be by distal or mesial for the filling by dripping of fluid heatcurable acrylic. After it is cured, the pontic is ready to file and polish. (FIG. 32.24).

It can also be made a vertical middle nest without occlusal coating, leaving uncovered the vestibular face to put an entire retainer (FIG. 17 to and *b*.23). The filling by dripping of fluid heatcurable acrylic will be by lingual or palatine. After it is cured, it is finished by giving the palatine or lingual form and it is polished.

18) THE FIXED METAL BRIDGE MADE OF WHITE WAX WITH PLASTIC MASK AND WITH RETAINER.

It consist of the execution of a horizontal or vertical nest without occlusal coating depending on the position in which the bridge will be located, for its better finishing. The pillars of the fixed bridge have to be covered with coating. The gingival borders of the pontic have to be covered with rockplaster. (FIGS. 31 and 32. 43) and a grip with selfcurable acrylic has to be made for each plastic mask. The fixed metal bridge with plastic mask is placed in horizontal position (FIG. 8b.) so that the plaster of Paris covers all the bridge leaving free the vestibular plastic mask.

If we put the bridge in vertical position, we make a vertical half nest without occlusal coating, the vestibular plastic mask and the lingual or palatine wax faces have to be free (FIG. 16c.24) Allow the plaster of Paris to be harden, vaseline the vestibular face of both nests without touching the plastic mask, make with the stone plaster an entire retainer on the upper face of the horizontal nest without occlusal coating works that are finished on the original model and the boiling is made on the original model:
They are finished directly without the need of making nests with or without retainers those which are filled with the fluid heatcurable acrylic on the original model. After the curing, the original model can not be preserved anymore.

2) These works are finished in heatcurable acrylic and the boiling is made without the model. These are the works that are filled with the fluid heatcurable acrylic by dripping on the mask and they are removed from the original model to make the boiling. After the boiling they are replaced on the original model to give the dental form and polish them.

3) In the requested fast works the boiling is made on the second model:
If we want to preserve the original model, it is convenient to make two equal models of a same impression. The first model is the original and the second model is to be finished in heatcurable acrylic, that after being cured the second model is not conserved anymore, but we have the first model to be finished by giving the dental form and to be polished.

TECHNIQUE OF THE FASTS METHODS:

1) The works are cured with the original model:
For example on the finishing of an acrylic crown: The clean, opaqued veneer without rests of wax, is placed on the original model. The veneer is glued by palatine to the original model with a selfcurable acrylic drop (FIG. 33,42.) by the back side (lingual or palatine, so that the veneer is not moved from its place neither during the filling by dripping of fluid heatcurable acrylic, or during the boiling.
The plastic mask is put on the vestibular face (FIG. 33.1). The mask is glued with pink wax by the incisals borders (FIG. 33.45) to hold it. It is filled with the fluid heatcurable acrylic by dripping by the distal side with the aid of a vibrator until it overflows by the opposite mesial side, (FIG. 33.24) immediately a small cotton roll is held, that it is placed by mesial to stop the exit of the fluid heatcurable acrylic until the space between the mask and the metal is filled completely. Stir up the heatcurable acrylic to eliminate air bubbles (with the top from a pin.). It is removed from the vibrator and is allowed to rest a little in lateral position so that the acrylic does not overflows from the place until it is hardened and then it is cured. After the boiling, it is cooled, the acrylic crown is removed and it is filed and polished.

If it it will not have mask it is worked in the same form, but filling by dripping of fluid heatcurable acrylic will be by vestibular. (FIG. 33.24)

If fixed metal bridges are requested, they are worked as the acrylic crowns.

2) The works are cured without the original model:
In special cases if it is wish to preserve the original model (wetted) can be filled with the heatcurable acrylic by dripping and once it has hardened, it is submerged inside of a cup with water at room temperature, allow to rest for five minutes, the work with the model is removed. With attention the work is removed from the original model, to be cured. After it is cured, it is put back again on the model to finish the filing and polishing.

3) The works are cured with the second model:
Other example Lo finish the acrylic part of an acrylic crown or of a fixed metal bridge in which it is convenient to make two equal models in rockplaster of a same impression: the first model is the definitive and the second is to fill with the fluid heatcurable acrylic by dripping and it is given the form cured with the model. After the boiling the acrylic crown or the fixed metal bridge is removed from the second model, the rockplaster excess are eliminated to be able to place it on the first definitive model, and it is finished by giving the dental form and then is polished.

FOR THE ACRYLIC CROWNS with gingival metal shoulder:
The advantage of this method is that the mask with the acrylic crowns already opaqued with metallic shoulders can be filled by dripping with heatcurable acrylic without using the die and without making a nest for the curing. After it is cured, it is finished by giving the form watching the neighboring teeth.

TECHNIQUE OF MIXED NESTS:
To make the simultaneous combined horizontal and vertical nests called "mixed nests" which are for fixed metal bridges that will have or have not masks and will have or have not retainers.
For example:
For a bridge of several pieces whose first pillar is a jacket (over metal) with a mask, the acrylic crown with plastic mask of the intermediate section, and the last pillar is a pivot with or without a mask.
For the jacket and an acrylic crown with a mask, a horizontal nest without occlusal coating (FIG. 34.18) is made leaving free the vestibular faces that will have entire retainer with a third of uncovered face and for the pivot with or without mask a vertical nest is made leaving free the occlusal face, combined on the same model.(FIG. 34)

The upper face of the multiple horizontal nest has to be vaselined to make retainers. For the jacket it has to be done an entire retainer with a third of uncovered face by distal or mesial for the filling by dripping of fluid heatcurable acrylic (FIG. 34.24). It is necesary to put vaseline by the distal or mesial side of the first retainer in order to continue making the other entire retainer on the veneer of the intermediate section leaving a third of uncovered face.

The filling by dripping of fluid heatcurable acrylic of the jacket and the intermediate section is by distal or mesial. The entire vertical nest does not needed a retainer. (FIG. 34.21).

The filling by dripping of fluid heatcurable acrylic for the vertical nest is made by occlusal.

When making the washing to eliminate the white wax, it is necessary to verify that the retainers be separated of the nests to eliminate totally the white wax and to opaque all the metal faces which had had a mask and allow to dry. the retainers are placed on the right positions glueing with cianoacrylate drops. It is necessary to prepare a portion of fluid heatcurable acrylic to fill through the hollow of the entire retainer with the jacket and it is allowed to harden. A small portion of fluid heatcurable acrylic is prepared again to fill through the hollow of the free third part of the entire retainer of the intermediate section and is allowed to harden. Finally more fluid heatcurable acrylic is prepared again to fill the vertical nest by occlusal and is allowed to harden and cured immediately.

After the curing, the bridge of the mixed nest is eliminated and it is finished by filing and polished.

For the works that will not have a plastic mask; there are made horizontal nests without occlusal coating that do not need retainers. The hollow for the filling by dripping of the fluid heatcurable acrylic is by vestibular and the hollow of entire vertical nest is only by occlusal. After the curing, the bridge is removed from the mixed nest and the uncovered vestibular faces are filed to give the dental forms and are polished as usual.

We claim:

1. A method for preparing a permanent dental acrylic part for a tooth restoration comprising using a temporary tooth made in wax finishing to obtain an impression of the tooth in rock plaster, filling the impression with heat-curable acrylic, and heat curing the acrylic all without the use of a dental flask.

2. A method as claimed in claim 1 wherein the heat-curable acrylic of at least one member selected from the group consisting of jackets, pivots, bridges, and crowns is heat cured without the use of a dental flask.

3. A method as claimed in claim 2 wherein said impression is made in a rock plaster nest.

4. A method as claimed in claim 3 wherein the nest is at least one horizontal nest, at least one vertical nest or a combination of at least one horizontal nest and at least one vertical nest.

5. A method as claimed in claim 2 wherein the heat-curable acrylic is polymerized in four stages of polymerization prior to its final curing.

6. A method as claimed in claim 1 wherein the heat-curable acrylic is dripped directly into said impression.

7. A method as claimed in claim 2 wherein the heat-curable acrylic is heat cured in 5 to 15 minutes.

8. A method as claimed in claim 3 wherein retainers of plaster complement the nest to maintain a plastic mask, hooks marks, dental morphology and the vertical dimension of the acrylic dental piece.

9. A method as claimed in claim 3 wherein a plurality of nests containing different permanent acrylic dental parts are simultaneously heat cured in a curing container at the same temperature and pressure for the polymerization of white, heat-curable acrylic or different shades of white heat-curing acrylic.

10. A method for producing a dental part comprising heat-cured acrylic which is permanently installed in the mouth comprising forming rock plaster into a nest, said nest comprising an open cavity, inserting a wax dental part into the cavity and pressing it into the surface of the rock plaster to make an impression of the wax dental part in an inside surface of the nest, removing the wax from the nest, dripping or pouring fluid heat-curable acrylic into the cavity of the nest so that it fills the impression left by the wax dental part, and heat curing the heat-curable acrylic in the nest without the use of a dental flask.

11. A method as claimed in claim 10 wherein said acrylic dental part is at least one member selected from the group consisting of jackets, pivots, fixed bridges, and crowns.

12. A method as claimed in claim 10 wherein said heat curing comprises:
heating water held in a pressure vessel to a temperature sufficient for heat curing of said acrylic dental part,
submerging said plaster nest containing said heat-curable acrylic in water within a curing container without a dental flask, and
heating the water in said curing container with the heated water held in said pressure vessel to heat cure said acrylic within said pressure vessel without a dental flask to obtain said acrylic dental part.

13. A method as claimed in claim 12 wherein the water held in said pressure vessel is heated to a temperature of 90° C. to 100° C. and the plaster nest is submerged in ambient temperature water within said curing container.

14. A method as claimed in claim 12 wherein said heat curing is conducted at a pressure of 3.5 bars.

15. A method as claimed in claim 12 wherein said curing container is supported on a table within said vessel so that the top edge of the curing container is above the level of said heated water held by said vessel.

16. A method as claimed in claim 15 wherein said table is perforated for circulation of said heated water around said curing container.

17. A method as claimed in claim 1 wherein said heat curing comprises:
a) providing a vessel for boiling or heating water, said vessel having an open top, a lid for sealing the top, an inlet for injection of compressed air into the vessel, an outlet for exhausting of compressed air, and valve means for closing and opening said inlet and said outlet,
b) heating water held in said vessel to a temperature sufficient for heat curing of said acrylic dental part,
c) placing said plaster containing the heat-curable acrylic into a curing container without a dental flask, and filling said curing container with water to cover said plaster, said curing container having an open top,
d) then placing the open curing container in said heated water such that the level of said heated water is below the open top of said curing container, and
e) pressurizing said vessel with compressed air, wherein said heated water held in said pressure vessel heats the water in said curing container to heat cure said acrylic dental part under pressure.

18. A method as claimed in claim 17 wherein said water in said vessel is heated to a temperature of 90° C. to 100° C. by said heating means.

19. A method as claimed in claim 18 wherein said curing container is filled with water at ambient temperature and said vessel is pressurized to a pressure of 3.5 bars.

20. A method as claimed in claim 17 wherein said acrylic dental part is a jacket, pivot, bridge, or crown.

21. A method as claimed in claim 1 wherein said wax is white.

* * * * *